United States Patent
Schrader

(10) Patent No.: US 7,222,455 B2
(45) Date of Patent: May 29, 2007

(54) COMPOSITIONS AND METHODS FOR SUPPRESSING CRACKING AND WATER LOSS FROM CHERRIES

(75) Inventor: Lawrence E. Schrader, Wenatchee, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 10/703,105

(22) Filed: Nov. 6, 2003

(65) Prior Publication Data

US 2004/0146617 A1 Jul. 29, 2004

Related U.S. Application Data

(63) Continuation-in-part of application No. 09/830,529, filed as application No. PCT/US99/25350 on Oct. 26, 1999.

(60) Provisional application No. 60/424,392, filed on Nov. 6, 2002, provisional application No. 60/106,059, filed on Oct. 27, 1998.

(51) Int. Cl.
A01G 17/02 (2006.01)
A01G 17/06 (2006.01)
A01D 46/28 (2006.01)

(52) U.S. Cl. .................. 47/58.1 FV; 47/DIG. 11; 426/89

(58) Field of Classification Search .......... 47/58.1 FV, 47/20.1, 24.1, DIG. 6, DIG. 11
See application file for complete search history.

(56) References Cited

U.S. PATENT DOCUMENTS

| | | | | |
|---|---|---|---|---|
| 2,013,063 | A | * | 9/1935 | Miller ............... 427/4 |
| 2,057,413 | A | | 10/1936 | Bridgeman et al. |
| 2,128,973 | A | | 9/1938 | Tisdale et al. |
| 2,198,991 | A | * | 4/1940 | Dutton ............... 427/4 |
| 3,847,641 | A | * | 11/1974 | Cushman et al. ........ 427/4 |
| 3,869,414 | A | | 3/1975 | Campbell |
| 4,058,409 | A | | 11/1977 | Kesslin |
| 4,082,558 | A | * | 4/1978 | Nobuo .............. 106/10 |
| 4,094,845 | A | * | 6/1978 | De Long ............ 524/512 |
| 4,756,922 | A | * | 7/1988 | Motoyama et al. ...... 427/4 |
| 4,793,850 | A | * | 12/1988 | Koester et al. ....... 504/363 |
| 4,802,305 | A | | 2/1989 | Kojimoto et al. |
| 4,882,874 | A | | 11/1989 | Paulson et al. |
| 4,946,694 | A | | 8/1990 | Gunnerson et al. |
| 5,049,186 | A | | 9/1991 | Kawabata |
| 5,165,915 | A | | 11/1992 | Tokubo et al. |
| 5,283,060 | A | | 2/1994 | Shieh |
| 5,296,226 | A | | 3/1994 | Askham |
| 5,306,488 | A | | 4/1994 | Vanlerberghe et al. |
| 5,733,531 | A | | 3/1998 | Mitchnick et al. |
| 5,908,708 | A | | 6/1999 | Sekutowski et al. |
| 6,027,740 | A | | 2/2000 | Puterka et al. |
| 6,036,765 | A | | 3/2000 | Farrow et al. |
| 6,069,112 | A | | 5/2000 | Glenn et al. |
| 6,110,867 | A | | 8/2000 | Glenn et al. |
| 6,156,327 | A | | 12/2000 | Sekutowski et al. |
| 6,235,683 | B1 | | 5/2001 | Glenn et al. |
| 6,464,995 | B1 | | 10/2002 | Sekutowski et al. |

FOREIGN PATENT DOCUMENTS

| | | | |
|---|---|---|---|
| DE | 1492835 | B | 7/1969 |
| GB | 2011788 | A | 7/1979 |
| JP | 50-21382 | | 7/1975 |
| JP | 58024502 | A * | 2/1983 |
| WO | WO 96/23413 | * | 8/1996 |
| WO | WO 98/38848 | A1 | 9/1998 |

OTHER PUBLICATIONS

Drake, S.R., et al., "'Bing' Sweet Cherry (*Prunus avium* L.) Quality as Influenced by Wax Coatings and Storage Temperature," *J. Food Sci.* 53(1):124-126 & 156, 1988.

Lidster, P.D., "Some Effects of Emulsifiable Coatings on Weight Loss, Stem Discoloration, and Surface Damage Disorders in 'Van' Sweet Cherries," *J. Amer. Soc. Hort. Sci.* 106(4):478-480, 1981.

* cited by examiner

*Primary Examiner*—Andrea M. Valenti
(74) *Attorney, Agent, or Firm*—Whitham Curtis Christofferson & Cook, PC

(57) ABSTRACT

In one aspect, the present invention provides methods for suppressing cracking, stem browning, and water loss in fruit or vegetables, such as cherries. The methods comprise applying to fruit or vegetables an amount of a wax emulsion effective to suppress cherry cracking, stem browning, and water loss. The wax emulsion used in the methods of the invention typically comprises a matrix of complex hydrocarbons, one or more emulsifying agents, and water. In some embodiments, the wax emulsion comprises from about 0.125% to about 25% (weight/weight) of carnauba wax, from about 0.1% to about 16% (weight/weight) of oleic acid, and from about 0.03% to about 6% (weight/weight) of morpholine, and from about 53% to about 99.7% (weight/weight) of water. In some embodiments, the wax emulsions further comprise one or more osmoregulators.

15 Claims, No Drawings

COMPOSITIONS AND METHODS FOR SUPPRESSING CRACKING AND WATER LOSS FROM CHERRIES

CROSS-REFERENCES TO RELATED APPLICATIONS

This application claims the benefit of U.S. Provisional Application No. 60/424,392, filed Nov. 6, 2002, and is a continuation-in-part of U.S. application Ser. No. 09/830, 529, filed Jul. 30, 2001, which is the National Stage of International Application No. PCT/US/99/25350, filed Oct. 26, 1999, which claims the benefit of U.S. Provisional Application No. 60/106,059, filed Oct. 27, 1998.

FIELD OF THE INVENTION

The invention relates to protective coated fruits and vegetables, and methods for the treatment of plants that reduces the incidence of insect and sunburn damage. The invention also relates to methods and compositions for suppressing cracking, stem browning, and water loss in fruit and vegetables, particularly cherries.

BACKGROUND OF THE INVENTION

Sunburn has been a problem for apple growers for at least 75 years, but its incidence has increased in recent years with the widespread use of dwarfing rootstocks and high-density plantings. Many cultivars (e.g., 'Fuji,' 'Granny Smith,' 'Jonagold,' 'Gala,' and 'Braeburn') are susceptible to sunburn. Prominent growers have indicated that sunburn may be the most significant cullage or quality problem in the industry. Trees are smaller and fruit are more exposed to solar radiation making fruit more susceptible to sunburn.

There is no adequate product on the market today for preventing sunburn damage. Many growers use overhead evaporative cooling or shadecloth to reduce sunburn in their apple orchards. Evaporative cooling decreases the temperature of the fruit and helps protect the fruit from sunburn (Parchomchuk, P. and Meheriuk, M., "Orchard cooling With Pulsed Overtree Irrigation to Prevent Solar Injury and Improve Fruit Quality of 'Jonagold' Apples," *HortScience* 31:802–804 (1996)). However, growers are concerned about several deleterious effects on fruit trees and soil (Warner, G., "Overhead Cooling May Not Be Total Sunburn Cure," *Good Fruit Grower* 46(12):20–21 (1995)). The shadecloths cost several thousand dollars per acre to install, and frequently interfere with normal color development of fruit. Uniform shade causes an undesirable alteration in the growth habit of apple trees and significantly reduces fruit production (Warner, G., "Cooling Problems Prompt Growers To Try Covers," *Good Fruit Grower* 46(12):24–25 (1995); Warner, G., "Growers Test Shade Cloths To Reduce Fuji Sunburn," *Good Fruit Grower* 46(17):55–63 (1995); Warner, G., "What Shade Do Cloths Provide, What Do You Need?", *Good Fruit Grower* 46(17):50–53 (1995)). Problems with these approaches confirm that new treatments are needed to lower fruit temperature, but not interfere with color development or fruit production.

In 1986 and 1987, Sibbett et al. ("Effect Of A Topically Applied Whitener On Sun Damage To Granny Smith Apples," *California Agriculture* 45(1):9–10 (1991)) in California attempted to solve the problem by applying a commercial whitener (Sunguard) to Granny Smith apples. The whitener had been developed for walnuts. They concluded from their experiments that Granny Smith apples could not be protected from sunburn by up to four topical applications of this particular whitening agent.

Miller Chemical & Fertilizer Corp. (Hanover, Pa.) markets an anti-transpirant concentrate called VAPOR GARD, and claims in its advertisements that the product reduced sunburn cullage by 30% in their trials. Transpiration is important to plant leaves, as evapotranspiration serves to cool the leaves and protects the leaves from heating to temperatures that are deleterious. Fruits have much lower transpiration rates than do leaves, but it seems likely that applying an anti-transpirant to fruit would exacerbate a situation in which there is already too much thermal energy.

Myhob, Guindy, and Salem in Egypt (*Bulletin of Faculty of Agriculture*, University of Cairo, 47(3):457–469 (1996)) reported that Agricultural GatCool significantly reduced sunburn as compared to controls sprayed with water on Balady mandarin fruits. duToit in South Africa (*Citrus and Subtropical Fruit Research Institute Information Bulletin No.* 80:8–9 (1979)) reported that spraying Koolcote on pineapple trees decreased fruit flesh temperatures by 2–3 degrees Celsius.

Lipton and Matoba (*HortScience* 6(4):343–345 (1971)) reduced sunburn of 'Crenshaw' melons by whitewashing fruit with a suspension of aluminum silicate.

Ing (*Good Fruit Grower* 49(6):58 (1998)), commenting on unpublished field trials, reports that the application of kaolin to apple fruits not only acts as an insect repellent, but also lowers canopy temperature, increases fruit size, and may reduce sunburn. However, as noted by 1 ng, application of kaolin to fruit surfaces is problematic. To achieve an insecticidal result, large amounts of kaolin (50 to 100 pounds per acre) must be applied to the fruit trees. Current kaolin formulations are reported to suffer from substantial application problems such as excessive foaming and "globbing" in spray tanks. (*Good Fruit Grower* 49(6):58 (1998)). Furthermore, kaolin powders are easily washed off by rain, thus necessitating multiple applications in order to maintain beneficial effects. (*Good Fruit Grower* 49(6):58 (1998); see also *Washington State University Cooperative Extension Area Wide IPM Update* 3(4): 1(1998)).

Sekutowski et al. (U.S. Pat. No. 5,908,708) developed a protective water resistant coating that was formulated as an aqueous dispersion of particulate matter having a hydrophobic outer surface in a low boiling point organic liquid, such as methanol. The particulate matter of the Sekutowski et al. coating can be any finely divided hydrophobic particulate solids including minerals, such as calcium carbonate, mica, talc, kaolin, bentonites, clays attapulgite, pyrophyllite, wollastonite, silica, feldspar, sand, quartz, chalk, limestone, precipitated calcium carbonate, diatomaceous earth and barytes. One agricultural use of the Sekutowski et al. aqueous dispersions is to provide tree leaves with a water resistant coating by spraying the formulation onto the surface of the leaves. The water resistant coating is thought to reduce plant disease and insect damage. However, one major problem with the Sekutowski et al. formulation is the use of large volumes of organic liquids such as alcohols, ketones and cyclic ethers that are highly flammable and pose other health risks to workers during spray application.

Protective formulations which additionally function as pesticides in plant crops would be a valuable addition to Integrated Pest Management (IPM) practices providing "soft" suppression of pests without disrupting natural control processes. Desirable formulations would be expected to be non-toxic to mammals and thus safe for applicators and farm workers. Application of the protective formulations by commonly employed horticultural spray operations invariably involves treatment of foliage and fruit or vegetable. It is therefore important to develop new formulations that have protective properties against sunburn to fruits and vegetables as well as against damage caused by insects that inhabit both foliage and fruit.

Rain-induced cherry cracking is one of the most serious problems to the sweet cherry industry around the world. Cracking of cherries induced by rain is often the greatest single cause of fruit cullage. Cherry cracking has been studied for several decades (Verner & Blodgett (1931) *Univ. Idaho Agr. Expt. Sta. Bull.* 184; Verner (1938) *Proc. Amer. Soc. Hort. Sci.* 36:271–74, Verner (1939) *Proc. Wash. State Hort. Assoc.* 35:54–57; Ackley (1956) *Inst. Agr. Sci. State Coll. of Wash. Expt. Publ.* 53; Christensen (1972) *Acta Agr. Sand.* 22:153–161; Andersen & Richardson (1982); Glenn & Poovaiah (1989) *J. Amer. Soc. Hort. Sci.* 114:781–788; Beyer et al. (2002) *Hort. Sci* 37(4): 637–641), but the phenomenon is not yet well understood.

It is generally thought that cherry cracking occurs as a result of direct water absorption through the fruit skin (Kertesz & Nebel (1935) *Plant Physiol.* 10:763–777; Verner (1939) *Proc. Wash. State Hort. Assoc.* 35:54–57; Westwood & Bjomstad (1970) *Proc. Oregon Hort. Soc.* 61:70–75; Christensen (1972) *Acta Agr. Sand.* 22:153–161; Beyer & Knoche (2002) *J. Amer. Soc. Hort. Sci.* 127(3):325–332; Beyer et al. (2002) *Hort. Sci.* 37(4): 637–641). Consequently, factors affecting permeability of the skin are of major importance in determining fruit resistance to water injury. Penetration of the cuticle, which occurs by diffusion or by mass flow through cuticular cracks and other surface structures, may be important in determining whether cherries are susceptible to cracking (Anderson & Richardson (1982) *J. Amer. Soc. Hort. Sci.* 107:441–444; Glenn & Poovaiah (1989) *J. Amer. Soc. Hort. Sci.* 114:781–788). Calcium is known to decrease hydraulic permeability of cell membranes and is reported to decrease water absorption in sweet cherries (Verner (1939) *Proc. Wash. State Hort. Assoc.* 35:54–57).

Some treatments have been demonstrated to reduce cherry cracking in some instances (see, e.g., Verner (1939) *Proc. Wash. State Hort. Assoc.* 35:54–57; Callan (1986) *J. Amer. Soc. Hort. Sci.* 111(2):173–175; Lang & Hayden (1996) *Proc. Wash. State Hort. Assoc.* 92:283–28; Lang et al. (1997) *Good Fruit Grower* 48(12):27–30; Fernandez & Flore (1998) *Acta Horticulturae* 468:683–689; Lang et al. (1998) *Acta Horticulturae* 468:649–656; Lang & Flore (1999) *Good Fruit Grower* 50(4):34–38; Heacox (2001) *Fruit Grower* 121(4):16). However, the applicability of these treatments in cherry production is limited due to variable or inconsistent results, mechanical problems, or phytotoxicity related to repeated applications (see, e.g., Koffman et al. (1996) *Plant Protec. Quart.* 11(3):126–30). Part of the variability in results has been attributed to differences in temperature at various sites, as temperature strongly influences natural fruit cracking (i.e., higher temperatures induce more cracking). In addition, cultivars appear to differ in their susceptibility to rain-induced cracking (King & Norton (1987) *Fruit Varieties J.* 41:83–84; Lang et al. (1997) *Good Fruit Grower* 48(12):27–30).

Fruit coating waxes have been used on many crops including apples, avocados, citrus, cucumbers, eggplant, peaches, sweet peppers, and tomatoes (Hagenmaier & Shaw (1992) *J. Amer. Soc. Hort. Sci.* 117(1):105–109). Many studies have investigated water loss during storage (Hagenmaier & Shaw (1992) *J. Amer. Soc. Hort. Sci.* 117 (1): 105–109. One study investigated the effects of antitranspirants and wax coatings that contained vegetable oil emulsions, shellac emulsions, or polysaccharide-protein-oil emulsions on cherries (Lidster (1981) *J. Amer. Soc. Hort. Sci.* 106:478–480). Some treatments reduced water loss after harvest, however, the antitranspirant treatments were deemed to be unacceptable for commercial use as they left an objectionable sticky residue.

In summary, there is a lack of adequate means to prevent sunburn and insect damage to fruit and vegetable crops. Thus, there is a strong need in agricultural markets for an inexpensive and effective composition that prevents sunburn, repels deleterious insects, is long lasting, and is relatively amenable to easy application by growers and commercial applicators. There is also a need for reliable methods for protecting cherries from the damaging effects of rainfall and for commercially acceptable methods for suppressing water loss from cherries.

SUMMARY OF THE INVENTION

It has now been discovered that the foregoing problems can be overcome and that sunburn in apples, and other fruit and vegetable crops requiring exposure to high intensity solar irradiance for maturation, can be significantly reduced by treating the crop with an effective amount of a plant protective coating composition of the present invention. An effective amount of a plant protective coating composition of the invention is defined as any amount of the inventive composition that upon application to the surface of a fruit or vegetable, results in the measurable reduction of the incidence of fruit or vegetable sun damage. The plant protective coating compositions of the invention also forms a barrier that reduces insect inflicted damage to the fruit or vegetable.

In a first aspect, the present invention provides a fruit or vegetable that is protectively coated with a plant protective composition comprising lipophilic thixotropic smectic clay suspended in a wax emulsion. In a second aspect, the present invention provides methods and compositions for protecting fruit and vegetables from sunburn and insect-inflicted damage. The methods comprise treating a fruit or vegetable with a sunburn preventative amount of a plant protective composition comprising lipophilic thixotropic smectic clay and a wax emulsion. The wax emulsion preferably comprises complex hydrocarbons (also known as a matrix of hydrocarbons), at least one emulsifying agent and water. In a presently preferred embodiment of the present invention, both an anionic lipophilic hydrophilic emulsifier and a cation hydrophilic emulsifier are used to emulsify the matrix of hydrocarbons. Preferably, the protective composition is a mixture of about 0.5 to 10% (weight/weight) of lipophilic thixotropic smectic clay dispersed in about 90 to 99.5% (weight/weight) of the wax emulsion. For some uses of the inventive composition it is preferable to dilute the mixed composition into an aqueous solution. Preferably, the compositions of the invention are diluted into an aqueous solution in a volume/volume ratio of about 1 part plant protective composition to about 1 to 40 parts aqueous solution such as about 1 part plant protective composition to about 10 parts aqueous solution.

Preferred plant protective coating compositions are sprayable onto fruit trees, vegetable crops and the like by a wide variety of commercial agricultural applicators. The matrix of hydrocarbons helps to maintain the physical integrity of the clay film on the fruit surface making the formulation more durable and resistant to rain wash. Because the plant protective coating compositions, when applied as finely dispersed spray particles, cover both foliage and fruit, a dual beneficial effect is achieved through prevention of the incidence of sunburn and damage by insects. The physical integrity of the clay film, as well as the matrix of hydrocarbons on foliage and fruit surfaces also provide an effective protective barrier against harmful insects which may naturally reside on both foliage and fruit.

In the practice of the invention, proper dilution of the inventive composition in an aqueous solution allows effective spray application of the sun and insect protective material on to fruits or leaves prior to conditions that lead to the incidence of fruit sunburn or insect damage. The inventive composition is preferably sprayed onto plants at a rate of about 50 to 500 gallons per acre, such as about 100 to 400 gallons per acre. As compared to other formulations and treatments used to prevent sunburn damage of fruits, the inventive compositions and methods of application significantly reduce the incidence of fruit sunburn damage resulting in both fruit necrosis and browning.

The inventive compositions and methods are applicable to a wide variety of fruits and vegetables including, for example, apples, pears, tomatoes, peppers, curburbits, honeydew melons, cantaloupes, avocados, plums, beans, squashes, peaches, grapes, strawberries, raspberries, gooseberries, bananas, oranges, tulips, onions, cabbages, and other. See, for example, Brooks, C. and Fisher, D. F., "Some High-Temperature Effects in Apples: Contrasts in the Two Sides of an Apple," *J. Agr. Res.* 32(1):1–16. (1926); Ware, W. M., "High Temperature Injury on the Growing Apple," *Gardners Chron.* 92:287–288 (1932); Meyer, A., "Comparative Temperatures of Apples," *Proc. Amer. Soc. Hort. Sci.* 28:566–567 (1932); Whittaker, E. C. and McDonald, S. L. D., "Prevention of Sunscald of Deciduous Fruit Trees in Hot Climates," *Agr. Gaz. N. S. Wales* 52:231–233 (1941); Moore, M. H. and Rogers, W. S., "Sunscald of Fruits," *East Malling Res. Sta. Report, Pp.* 50–53. (1943); Cook, M. T., "Sunburn and Tomato Fruit Rots," *Phytopathologyy* 11:379–380 (1921); Harvey, R. B., "Sunscald of Tomatoes," *Minn. Studies Plant Sci.* 4:229–234 (1924); Harvey, R. B., "Conditions for Heat Canker and Sunscald in Plants," *J. Forestry* 23:292–294 (1925); Ramsey, G. B. and Link, G. K. K., "Market Diseases of Fruits and Vegetables: Tomatoes, Peppers and Eggplants," *U. S. Dept. Agr., Misc. Publ.* 121:28–29 (1932); Moore, M. H. and Rogers, W. S., "Sunscald of Fruits," *East Malling Res. Sta. Report,* Pp. 50–53. (1943); Retig, N. and Kedar, N., "The Effect of Stage of Maturity on Heat Absorption and Sunscald of Detached Tomato Fruit," *Israel J Agr. Res.* 17:77–83 (1967); Kedar, N. and Retig, N., "An Oblong Dwarf Tomato Resists Sunscald," *New Scientist* 36:546 (1967); Weber, G. F., "Diseases of Peppers in Florida," *Florida Univ. Agr. Expt. Sta. Bull.* 244:35–37 (1932); Bremer, H., "On Pod Spots in Peppers," *Phytopathology* 35:283–287 (1945); Barber, H. N. and Sharpe, P. J. H., "Genetics and Physiology of Sunscald of Fruits," *Agr. Meterol* 8:178–191 (1971); Rabinowitch, H. D., Friedmann, M., and Ben-David, B., "Sunscald Damage in Attached and Detached Pepper and Cucumber Fruits at Various Stages of Maturity," *Scientia Hort.* 19:9–18 (1983); Rabinowitch, H. D., Ben-David, B., and Friedmann, M., "Light is Essential for Sunscald Induction in Cucumber and Pepper Fruits, Whereas Heat Conditioning Provides Protection," *Scientia Hort.* 29:21–29 (1986); Leclerg, E. L., "The Relation of Leaf Blight to Sun Scald of Honeydew Melons," *Phytopathology* 21:97–98 (1931); Lipton, W. J., "Ultraviolet Radiation as a Factor in Solar Injury and Vein Tract Browning of Cantaloupes," *J. Amer. Soc. Hort. Sci* 102:32–36 (1977); Schroeder, C. A. and Kay, E., "Temperature Conditions and Tolerance of Avocado Fruit Tissue," *Calif Avocado Soc. Yearbook* 45:87–92 (1961); Renquist, A. R., Hughes, H. G. and Rogoyski, M. K., "Solar Injury of Raspberry Fruit," *HortScience* 22:396–397 (1987); Maxie, E. C. and Claypool, L. L., "Heat Injury in Prunes," *Proc. Amer. Soc. Hort. Sci.* 69:116–121 (1956); Farmer, A., "Sunscald of Japanese Plum Fruits," *Orchardist New Zealand* 51:113–114 (1968); Macmillan, H. G., "Sunscald of Beans," *J. Agr. Res.* 13:647–650 (1918); Macmillan, H. G., "Cause of Sunscald of Beans," *Phytopathology* 13:376–380 (1923); Macmillan, H. G. and Byars. L. P., "Heat Injury to Beans in Colorado," *Phytopathology* 10:365–367 (1920); Ramsey, G. B. and Wiant, J. S., "Market Diseases of Fruits and Vegetables: Asparagus, Onions, Beans, Peas, Carrots, Celery, and Related Vegetables," *U.S. Dept. Agr., Misc. Publ.* 440: 17–32. (1941); Ramsey, G. B., Wiant, J. S. and Link., G. K. K., "Market Diseases of Fruits and Vegetables: Crucifers and Cucurbits," *U.S. Dept. Agr., Miscl Publ.* 292:20 (1938); Rhoads, A. S., "Sun-scald of Grapes and its Relation to Summer Pruning," *Amer. Fruit Grower* 44:20–47 (1924); Graves, A. H., "Sunscald of Tulip Flowers," *Phytopathology* 27:731–734 (1937); Green, G. C., "The Banana Plant. In: The Effect of Weather and Climate Upon the Keeping Quality of Fruit," *World Meteorological Organization, Technical Note No.* 53:113–135 Geneva (1963); Wade, N. L., Kavanagy, E. E. and Tan, S. C., "Sunscald and Ultraviolet Light Injury of Banana Fruits," *J. Hort. Science* 68:409–419 (1993), Ketchie, D. O. and Ballard, A. L., "Environments Which Cause Heat Injury to Valencia Oranges," *Proc. Amer. Soc. Hort. Sci.* 93:166–172. (1968). In addition, the plant protective compositions can be used on trees whose foliage is susceptible to sunburn, such as maples, basswood, boxelder, black walnut, birch, balsam fir, Douglas fir, Eastern white pine and spruce as well as many fruit trees (Litzow, M. and Pellett, H., "Materials for Potential use in Sunscald Prevention," *J. Arboriculture* 9:35–38 (1983); Green, S. B., "Forestry in Minnesota," *Geological and Natural History Survey of Minnesota, St. Paul* 401 pp. (1902); Huberman, M. A., "Sunscald of Eastern White Pine, *Pinus Strobus L.,*" *Ecology* 24:456–471 (1943)). The inventive methods and compositions can also be used on plants that are not susceptible to sunburn but which are impacted by insect damage. In addition to the above listed plants that are susceptible to sunburn and insect damage, the following plants would independently benefit from the insect protective qualities of the inventive plant protective composition: soybeans, potatoes, peas, lentils, apricots, cherries.

In a third aspect, the present invention provides methods and compositions for suppressing cracking, water loss, and/or stem browning of fruit and vegetables. In some embodiments, the methods of the third aspect of the invention are used for suppressing cracking, stem browning, and water loss from cherries. However, these methods are also applicable to other fruit and vegetables, including, but not limited to apples, pears, tomatoes, peppers, curburbits, honeydew melons, cantaloupes, avocados, plums, beans, squashes, grapes, strawberries, raspberries, gooseberries, bananas, onions, oranges and other citrus fruits. The methods for suppressing cracking, water loss, and/or stem browning each comprise applying to fruit or vegetables an amount of a wax emulsion effective to suppress cracking, water loss, and/or stem browning.

The wax emulsion used in this aspect of the invention typically comprises a matrix of complex hydrocarbons, one or more emulsifying agents, and water. In some embodiments, the one or more emulsifying agent comprises at least one anionic lipophilic emulsifying agent and at least one ionic hydrophilic emulsifying agent.

In presently preferred embodiments, the concentration of complex hydrocarbons in the wax emulsion of the invention is from about 0.125% to about 25% (weight/weight), and the concentration of emulsifying agent(s) is from about 0.1% to about 22% (weight/weight), such as from about 0.1% to about 10% (weight/weight). A representative wax emulsion of the invention may comprise, for example, from about 0.125% to about 25% (weight/weight) of carnauba wax, from about 0.1% to about 16% (weight/weight) of oleic acid, and from about 0.03% to about 6% (weight/weight) of morpholine, and from about 53% to about 99.7% (weight/weight) of water. Another representative wax emulsion of the invention may comprise, for example, from about 0.125% to about 25% (weight/weight) of carnauba wax, from about 0.1% to about 5% (weight/weight) of oleic acid, and from about 0.03% to about 5% (weight/weight) of morpholine, and from about 65% to about 99.7% (weight/weight) of water.

In other embodiments, the wax emulsions of the invention may further comprise from about 0.01% to about 5% (weight/weight) of an osmoregulator, such as, for example, a calcium salt (e.g., calcium chloride) or a potassium salt (e.g., potassium chloride), an amino acids (e.g., lysine), or a sugar (e.g., sucrose).

The methods of the invention provide an at least about 4-fold reduction in cherry cracking, a reduction in water loss from harvested cherries of at least about 50%, and a reduction of stem browning of about 30%.

DETAILED DESCRIPTION OF THE PREFERRED EMBODIMENT

Two types of sunburn exist in apples. One is a lethal phenomenon that leads to a necrotic area on the fruit. Such fruit becomes cullage. This phenomenon occurs when the sun-exposed side of apple skin reaches a temperature of 52°±1° Celsius for only 10 minutes. The second type of sunburn is a sublethal phenomenon that leads to a browning of the apple skin (sometimes referred to as "buckskin"). These apples can be sold, but at a lower grade and price.

Solar light contains ultraviolet, visible, and infrared radiation. All fruits and vegetables which develop a yellow or red coloration as part of their growth cycle require a certain quantity of ultraviolet and visible light to achieve the desired maturation color. Infrared light predominantly leads to excessive heating and associated damage to fruit surfaces. The plant protective compositions of the present invention selectively filter out the infrared portion of solar light but allow other light components to pass. The inventive clay coating is therefore invisible to the unaided eye. In contrast, kaolin based formulations appear on the surface of sprayed fruits and leaves as a whitish-gray dust, which uniformly reflects all components of solar light, therefore depriving the developing fruit of the beneficial aspects of solar light.

In a first aspect, the present invention provides a fruit or vegetable that is protectively coated with a composition comprising lipophilic thixotropic smectic clay and a wax emulsion. The wax emulsion comprises a matrix of complex hydrocarbons, at least one emulsifier agent and water. Preferably, the wax emulsion contains two emulsifying agents: an anionic lipophilic emulsifier and an ionic hydrophilic emulsifier. Preferably, each emulsifier is present in the wax emulsion at a concentration of between 1–15% (weight/weight).

In a second aspect, the present invention provides a method of protecting fruit and vegetables from sunburn, comprising treating a fruit or vegetable with a sunburn preventative amount of a plant protective composition comprising lipophilic thixotropic smectic clay and a wax emulsion. The wax emulsion is composed of a matrix of complex hydrocarbons, at least one emulsifier agent and water. Preferably, the composition is applied to the fruit or vegetable multiple times through the growing season.

In yet another embodiment of the invention a method of plant protection is provided, comprising treating a plant with an insect-controlling amount of a plant protective composition comprising lipophilic thixotropic smectic clay and a wax emulsion. The wax emulsion is composed of a matrix of complex hydrocarbons, at least one emulsifier agent and water.

The compositions and methods of the invention significantly decrease the incidence of both types of sunburn in apples. The plant protective compositions are preferably based on a thixotropic smectic clay material that is chemically altered to render its surface lipophilic. Thixotropic clays, in their original form are typically hydrophilic. In order to increase the ability of the protective compositions of the invention to adhere to the lipophilic surface of fruit, the clay is rendered lipophilic, such as, for example, by transformation by a chemical reaction of the clay with quaternary ammonium compounds in which the ligands consist entirely of aliphatic long-chain hydrocarbons or of a mixture of aliphatic and aromatic hydrocarbon residues. This reaction converts the hydrophilic clay into a hydrophobic and lipophilic material that is capable of molecularly dispersing oils, waxes and other lipid-like materials including organic solvents. Suitable thixotropic clay materials for use in the practice of the invention include clays that have been transformed by a chemical reaction of the clay with quaternary ammonium compounds and have a clay structure that weakens when subjected to shear forces and increases in strength upon standing. Many thixotropic smectic clays suitable for use in the practice of the present invention are commercially available through a variety of vendors.

Unless specifically defined herein, all terms used herein have the same meaning as they would to one skilled in the art of the present invention. As used herein, the term "plant protective composition" refers to a composition of the invention that protects fruits and vegetables from sunburn and/or insect damage. As used herein, the term "smectic clay" material refers to a Bentonite, platelet-type clay. When transformed to render it lipophilic, this clay may also be referred to as "organoclay".

The successful functioning of the inventive sunburn protectant requires a matrix consisting of complex hydrocarbons which renders the formulation sprayable by commercial agricultural applicators, maintains the physical integrity of the clay on fruit and allows passage of visible solar radiation needed for fruit color formation but reflects undesired solar infrared light. The wax emulsion is formed by emulsifying natural or synthetic waxes with at least one emulsifying agent. Preferably, both an anionic lipophilic emulsifier and an ionic hydrophilic emulsifier are used to emulsify the matrix of hydrocarbons. The wax emulsion in the protective compositions of the present invention is intended to replace and enhance the properties of the natural wax layer which exists on the surface of all fruits and vegetables.

As used herein, the term "matrix of complex hydrocarbons" refers to a lipid-based matrix. Suitable complex hydrocarbons for use in the present invention include, for example, natural and synthetic waxes that are suitable for human consumption, with melting temperatures that are higher than the melting temperatures of the natural waxes on target fruit or vegetables. In a presently particularly preferred embodiment, the complex hydrocarbons of the present application is Carnauba Wax of a tropical origin. It contains a mixture of true waxes with long chain fatty acids and long chain esters. The fatty acid composition is complex but well represented by the term "Carnauba Wax" (extracts of *Copernicia cerifera* Mart.). It will be apparent to those skilled in the art that other edible plant-derived waxes, such as Candelilla Wax (extracts from *Euphorbia cerifera* and *Pedilantus pavonis*), Alfa (extracts from *Stipa Tenacessima*), or mixtures thereof, will also be useful for this purpose. In addition, other natural wax mixtures well known in the art, such as montan wax, rice-bran wax, beeswax, Japan wax and mixtures thereof can also be used in the plant protective compositions of the present invention. It is also apparent that any edible synthetic waxes containing oxygen can also be used to practice the present invention. For example, oxidized microcrystalline wax and oxidized paraffin wax, secondary modified products thereof, and maleic waxes obtained by addition reactions between hydrocarbon waxes and maleic anhydride, can be used to practice the present invention. Oxygen-containing waxes can each be obtained by reacting 3–25 parts by weight of an unsaturated polycarboxylic acid or an anhydride thereof to 100 parts by weight of a hydrocarbon wax whose melting point is in a range of 50° C. to 85° C. See, for example, the description of synthetic oxygen containing waxes in U.S. Pat. No. 5,049,186, incorporated herein by reference. In compositions comprising a lipophilic thixotropic smectic clay, suitable matrices of complex hydrocarbons are those matrices of complex hydrocarbons that are capable of absorbing and dispersing the lipophilic organoclay.

The wax emulsion of the present invention is made by emulsifying the matrix of hydrocarbons with an amount of an emulsifying agent sufficient to emulsify the matrix of hydrocarbons. A large number of different emulsifying agents can be used to prepare the wax emulsion used in the practice of the present invention. Both cationic and anionic emulsifiers can be used. Exemplary emulsifiers include anionic surfactants, including salts of higher fatty acids such as myristic acid, stearic acid, palmitic acid, behenic acid, isostearic acid, oleic acid; with potassium, sodium, diethanolamine, triethanolamine, amino acid; the above alkali salts of ether carboxylic acids, salts of N-acylamino acids, salts of N-acylsarcosinic acids, salts of higher alkylsulfonic acids; cationic surfactants, including alkylamine salts, polyamines, aminoalcohol fatty acid organic silicone resins, alkyl quaternary ammonium salts. See for example the emulsifying agents described in U.S. Pat. Nos. 5,049,186 and 5,165,915, incorporated herein by reference. Preferably, both an anionic lipophilic emulsifier and an ionic hydrophilic emulsifier are mixed with the matrix of hydrocarbons in an amount sufficient to emulsify the edible waxes. Preferably, the anionic lipophilic and the ionic hydrophilic emulsifiers are each present in the wax emulsion at a concentration of between about 1–15% (weight/weight) relative to the matrix of hydrocarbons.

The anionic lipophilic surfactants employed in the practice of the invention have, preferably, a hydrophilic-lipophilic balance (HLB) ranging from 10 to 40. They are principally salts of fatty acids (for example alkaline salts or organic salts such as amine salts), the said fatty acids having, for example, from 12 to 18 carbon atoms, and being able to have a double bond as in the case of oleic acid; the alkaline salts or salts of organic bases of alkyl-sulfuric and alkyl-sulfonic acids having 12 to 18 carbon atoms, of alkyl-arylsulfonic acids whose alkyl chain contains 6 to 16 carbon atoms, the aryl group being, for example, a phenyl group. They are also ether-sulfates, in particular, the sulfatation products of fatty alcohols and polyalkoxylated alkylphenols, in which the aliphatic chain has from 6 to 20 carbon atoms and the polyalkoxylated chain has from 1 to 30 oxyalkylene units, in particular oxyethylene, oxypropylene or oxybutylene. Preferred anionic hydrophilic surfactants are the fatty acids oleic acid and stearic acid.

Presently preferred ionic hydrophilic surfactants include amine compounds such as ethanolamine, diethanolamine, triethanolamine, alkyl alcohol amines such as methyl-ethanolamine, butyl-ethanolamine, morpholene and mixtures thereof.

An exemplary wax emulsion for use as the wax emulsion in the composition of the present invention for protecting fruit and vegetables from sunburn and insect damage is APL-BRITE 310 C produced by Solutec Corporation (Yakima, Wash.). Other commercially available material suitable for use in the inventive protective coating composition are: Decco 231 produced by Elf-Atochem North America (Philadelphia, Pa.); Johnson's H. S and Johnson 31 produced by S. C. Johnson Wax (Racine, Wis.); and Shield Brite AP50C and Carnauba Gold produced by Pace International LLC (Seattle, Wash.).

A presently preferred material which meets the requirements specified for a chemically altered thixotropic smectic clay is Tixogel® MP 100 that can be commercially obtained from Sud-Chemie Rheologicals, a division of United Catalysts Inc. of Louisville, Ky. Tixogel® MP 100 is presently employed as an additive to a wide range of products including cosmetics, but not to our knowledge for any treatments of fruits or vegetables and not in combination with a matrix of complex hydrocarbons. A person with skill in the art will appreciate that many other organoclay materials having the required clay properties exist. Representative examples of useful clay materials include: numerous Tixogel and Optigel products, also produced by Sud-Chemie Rheologicals; the Bentone line of organoclays, obtainable from Rheox, Inc. (Highstown, N.J.); organoclays produced by Southern Clay Products (Gonzales, Tex.) and, the Vistrol and Organotrol lines of organoclays, sold by CIMBAR Performance Minerals (Cartersville, Ga.). The distinguishing property of the thixotropic organoclays used in the present invention is that they must be lipophilic.

For proper formulation of the inventive compositions for protecting fruit and vegetables from sunburn and insect damage it is essential to effect an activation of the organoclay (Tixogel® MP 100) with the wax emulsion (APL-BRITE 310 C) prior to dilution with water. A mixture of about 0.5 to 7% (weight/weight) Tixogel® MP 100 in APL-BRITE 310 C can be made at room temperature by mechanical stirring, but above about 7% (weight/weight) the mixture will quickly turn into a solid gel. Preferably, the plant protective composition is a mixture of about 5% (weight/weight) of Tixogel® MP 100 in about 95% (weight/weight) APL-BRITE 310 C. The resulting protective coating material contains thixotropic clay suspended in a sprayable wax emulsion. The ratio of thixotropic smectic clay to wax emulsion may change if products other than Tixogel® MP 100 or APL-BRITE 310C are employed as the organoclay and wax emulsion, respectively.

More generally, the composition of the present invention for protecting fruit and vegetables from sunburn and insect damage is a mixture of about 0.5 to 10% (weight/weight) lipophilic thixotropic smectic clay dispersed in about 90 to 99.5% (weight/weight) of the wax emulsion. Preferably, the plant protective composition is a mixture of about 3% to 7% (weight/weight) lipophilic thixotropic smectic clay dispersed in about 97 to 93% (weight/weight) of the wax emulsion. Most preferably, plant protective composition is a mixture of about 5% (weight/weight) lipophilic thixotropic smectic clay dispersed in about 95% (weight/weight) of the wax emulsion.

In the compositions for protecting fruit and vegetables from sunburn and insect damage, the wax emulsion generally comprises about 5% to about 25% (weight/weight), such as about 5% to 10% (weight/weight), natural wax or edible synthetic oxygen containing wax, about 2% to 30% (weight/weight) emulsifying agent and about 45% to about 93% (weight/weight), such as about 60 to 93% (weight/weight) water. Preferably, the emulsifying agent comprises about 1 to 15% (weight/weight) anionic lipophilic emulsifier, such oleic acid, and about 1 to 15% (weight/weight) ionic hydrophilic emulsifier, such as morpholene. When the anionic lipophilic emulsifier is oleic acid and the ionic hydrophilic emulsifier is morpholene, it is most preferable that morpholene be used at a molar ratio, relative to oleic acid, that is larger than about 1.0. Most preferably, the wax emulsion comprises about 5% to about 25% (weight/weight), such as 5 to 10% (weight/weight), natural wax selected from the group consisting of Carnauba wax, Candelilla wax, Alfa wax, montan wax, rice-bran wax, beeswax, Japan wax and mixtures thereof; about 2 to 7% (weight/weight) oleic acid, about 2 to 7% (weight/weight) morpholene and about 61 to 86% (weight/weight), such as 76 to 91% (weight/weight) water.

In some embodiments, the composition comprising a lipophilic thixotropic smectic clay and a wax emulsion may be prepared by first making a clay emulsion using the emulsifiers described above and then combining the clay emulsion with the wax emulsion. The wax may also be melted into the clay emulsion.

The composition for protecting fruit and vegetables from sunburn and insect damage can be applied directly onto plants or it may be diluted in an aqueous solution in any ratio which accommodates the desired field spray technique. Suitable ratios for use of the present invention include, for example, dilution of the protective coating mixture into an aqueous solution in a volume/volume ratio of about 1 part protective coating mixture to about 1 to 40 parts aqueous solution, such as about 1 part protective coating mixture to about 10 parts aqueous solution. In most applications for apple and pear fruit, the rate of spray volume may range from 50 to 500 gal/acre, such as about 100 to 400 gal/acre. The number of spray applications per growing season is also variable but ranges from one application up to ten applications depending upon weather conditions. A person skilled in the art will appreciate that the above mentioned rates would be expected to change to a minimal degree if the inventive composition were applied to other fruits and vegetables, except that there would be a greater variation in final mixture/water ratios due to the specific requirements of agricultural crops involved, i.e. row crops, perennial trees, etc.

In a third aspect, the present invention provides methods and compositions for suppressing cracking, water loss, and/or stem browning of fruit and vegetables. In some embodiments, the methods of the third aspect of the invention are used for suppressing cracking, stem browning, and water loss from cherries. However, these methods are also applicable to other fruit and vegetables, including, but not limited to apples, pears, tomatoes, peppers, curburbits, honeydew melons, cantaloupes, avocados, plums, beans, squashes, grapes, strawberries, raspberries, gooseberries, bananas, onions, oranges and other citrus fruits. The methods for suppressing cracking, water loss, and/or stem browning each comprise applying to fruit or vegetables an amount of a wax emulsion effective to suppress cracking, water loss, and/or stem browning. Thus, in some embodiments the invention provides methods for suppressing cherry cracking, comprising treating cherries with an amount of wax emulsion effective to suppress cherry cracking. The invention also provides methods and compositions for suppressing water loss from cherries, comprising applying to cherries an amount of a wax emulsion effective to suppress water loss. The invention further provides methods for suppressing stem browning, comprising treating cherries with an amount of wax emulsion effective to suppress stem browning.

The term "suppression of cracking" as used herein refers to any measurable decrease in the incidence, severity, or extent of cracking of fruit and vegetables. The term "suppression of water loss" as used herein refers to any measurable decrease in water loss from fruit or vegetables, such as a decrease in weight. The term "suppression of stem browning" refers to any measurable decrease in the incidence, severity, or extent of stem browning. Thus, a measurable decrease may refer to a complete elimination, a reduction in frequency or amount, or a delay in the onset of cracking, water loss, or stem browning.

The matrix of complex hydrocarbons suitable for use in the methods of the third aspect of the invention is a lipid-based matrix that is effective in suppressing cracking, water loss, and/or stem browning in fruit or vegetables. Suitable matrices of complex hydrocarbons include, but are not limited to natural and synthetic waxes, as described above. The wax emulsion of the third aspect of the invention may comprise from about 0.125% to about 25% (weight/weight) of complex hydrocarbons (such as carnauba wax), more preferably from about 0.5% to about 20% (weight/weight), and most preferably from about 2% to about 20% (weight/weight).

The wax emulsion is formed by emulsifying natural or synthetic waxes with an amount of at least one emulsifying agent sufficient to emulsify the matrix of complex hydrocarbons. A large number of different emulsifying agents can be used to prepare the wax emulsion used in the practice of the present invention, as described above. In some embodiments, both an anionic lipophilic emulsifying agent and an ionic hydrophilic emulsifying agent are mixed with the matrix of hydrocarbons in an amount sufficient to emulsify the edible waxes. The wax emulsion used in the third aspect of the invention typically comprises about 0.1% to about 22% (weight/weight) of emulsifying agent(s). In some embodiments, the anionic lipophilic emulsifying agent and the ionic hydrophilic emulsifying agent are each present in the wax emulsion at a concentration of from about 0.03% to about 16% (weight/weight).

Thus, the wax emulsion compositions used in the practice of the third aspect of the invention typically comprise about 0.125% to about 25% (weight/weight) of natural wax or edible synthetic oxygen wax, about 0.1% to about 22% (weight/weight) emulsifying agent(s), and about 53% to about 99.7% (weight/weight) water. In some embodiments, the emulsifying agent comprises about 0.1% to about 16% (weight/weight) of an anionic lipophilic emulsifying agent, such as oleic acid, and about 0.03% to about 6% (weight/weight) of an ionic hydrophilic emulsifying agent, such as morpholine. When the anionic lipophilic emulsifying agent is oleic acid and the ionic hydrophilic emulsifying agent is morpholine, the molar ratio of morpholine to oleic acid is typically larger than about 1.0. In some embodiments, the wax emulsion comprises about 0.125% to about 25% (weight/weight) natural wax selected from the group consisting of carnauba wax, candelilla wax, alfa wax, montan wax, rice-bran wax, beeswax, Japan wax, and mixtures thereof, about 0.1% to about 16% (weight/weight) oleic acid, about 0.3% to about 6% (weight/weight) morpholine, and about 53% to about 99.7% (weight/weight) water.

An example of commercially available wax emulsions for use in the third aspect of the invention includes C-Wax Emulsion (CH$_2$O Inc., Olympia, Wash.), which contains 10–20% refined carnauba wax, morpholine (<5%), and fatty acid (<5%) (Material Safety Data Sheet for C-Wax Emulsion, http://www.ch20.com/htmlmsds/35037445.htm). Another exemplary wax emulsion is NS 9000 (Pace International, Seattle, Wash.), which contains about 20% (w/v) carnauba wax and about 2–4% (volume/volume) each of morpholine and oleic acid.

The wax emulsion compositions of the third aspect of the invention may further comprise an osmoregulator. The term "osmoregulator" refers to a substance that increases the osmotic potential of the wax emulsion and thereby slows the uptake of water by fruit, such as cherries, or vegetables. Suitable osmoregulators include any osmoregulator known in the art that does not cause phytotoxicity. Thus, the osmoregulator used in the wax emulsions may be a calcium salt, for example calcium chloride, as shown in EXAMPLE 3. Other suitable calcium salts include calcium nitrate, calcium hydroxide, calcium acetate, Opti-Cal (Pace International, Seattle, Wash.), and Mira-Cal (Nutrient Technologies, La Habra, Calif.). The concentration of calcium salt in the wax emulsion is typically between about 0.01% to about 5% (weight/volume), such as between about 0.1% and 1%. Other suitable osmoregulators include, but are not limited to, salts that dissociate into monovalent cations and anions (e.g., potassium chloride or potassium nitrate) sugars (e.g., sucrose), amino acids (e.g., lysine) and boric acid. For example, potassium chloride may be used as an osmoregulator, for example, at a concentration of about 1% (w/v). In some embodiments, the wax emulsion comprises about 1% lysine as an osmoregulator.

The wax emulsion compositions of the third aspect of the invention may be applied undiluted or they may be diluted prior to application. For example, the wax emulsions may be diluted from about 4 to about 100 volumes of water prior to application. The preferred concentration of complex hydrocarbons such as carnauba wax applied is between about 0.2% and about 5% (weight/weight), such as between about 1% and about 5% or between about 2% and about 4%. The concentrations of emulsifying agents such as morpholine and/or oleic acid is preferably between about 0.1% to about 1.5% (weight/weight) each.

In some embodiments, a water softener may be added to the wax emulsion or when diluting the wax emulsions. Suitable water softeners include any agents that chelate divalent cations that make water hard. Exemplary water softeners include, but are not limited to, tetrasodium EDTA. In some embodiments, 26 ounces of 26% (w/v) tetrasodium EDTA are added per 100 gallons of water before diluting the wax emulsions. The water softener may also be incorporated into the wax emulsion.

The wax emulsions may be applied to fruit and vegetables at any time before or after harvest. For example, the wax emulsions may be applied to cherry trees during any stage of cherry fruit growth or when cherries are susceptible to cracking or before anticipated rain. For suppression of cracking, the wax emulsions are typically applied during the development or the ripening of the cherries close to maturity, for example, within two weeks of maturity. There may be a single application of the wax emulsions or the wax emulsions can be administered to the cherry trees in two, three, four, or more applications. The wax emulsion can be applied by any of the methods typically known and used in the agricultural industry for the application of a chemical, for example, by any common spraying technique used in the agricultural industry. For suppression of water loss or stem browning, the wax emulsions are typically applied at any time before or after harvest.

The wax emulsion compositions of the invention are applied to fruit or vegetables in an amount effective to suppress cracking, water loss, and/or stem browning. An amount of wax emulsion effective to suppress cracking, water loss, and/or stem browning is an amount sufficient to achieve a uniform coating of the fruit or vegetables. The effective amount of wax emulsion may depend on the method of application. For example, if applied using a speed sprayer (airblast sprayer), the amount of wax emulsion effective to suppress cherry cracking may be between about 100 and about 400 gallons per acre, and depends on the size of the trees. If applied using a low-volume sprayer with hydraulically-controlled nozzles and fans (e.g., a Proptec sprayer), the amount of wax emulsion effective to suppress cherry cracking may be around 50 gallons per acre. If applied using a helicopter, the amount of wax emulsion effective to suppress cherry cracking may be between about 5 to about 20 gallons per acre. Amounts of wax emulsion that are effective to suppress cherry cracking are generally also effective to suppress water loss and stem browning. Typically, the wax emulsions are applied to cherry trees to the point of runoff, i.e., to the point when the fruit and leaves are covered by the solution and excess begins to run off.

The methods of the invention can be used to suppress cherry cracking in any cultivar of cherries, such as 'Bing', 'Rainier', 'Sweetheart', 'Van', 'Lapins', 'Chelan', 'Tieton', and 'Liberty Bell'. Cracking of cherries is significantly reduced using the wax emulsions and methods of the invention. In some embodiments, the methods of the invention result in a delay in the appearance of cracked cherries as well as at least an about 3-fold reduction in the number of cracked cherries, as shown in EXAMPLE 12. Thus, application of a wax emulsion according to the invention two weeks before harvest results in at least an about 4-fold reduction in the number of cracked cherries, as described in EXAMPLE 15. Similarly, application of a wax emulsion according to the invention one week before harvest results in at least an about 2-fold reduction in the number of cracked cherries, as described in EXAMPLE 15. In some embodiments, the methods of the invention provide a reduction in water loss from harvested cherries. For example, application of a wax emulsion according to the invention to harvested cherries results in a water loss reduction of at least about 30%, as shown in EXAMPLE 14, or about 50% as described in EXAMPLE 17. Moreover, application of a wax emulsion according to the invention provides an increase in the firmness of cherries after storage, as described in EXAMPLE 17.

Some embodiments of the invention provide suppression of stem browning. For example, application of a wax emulsion according to the invention before harvest results in a reduction of stem browning of about 30%, as shown in EXAMPLE 17. Additionally, application of a wax emulsion according to the invention after harvest results in a reduction of stem browning of about 7%, as shown in EXAMPLE 17

In a fourth aspect, the invention provides a fruit or vegetable, such as a cherry, that is protectively coated with an amount of wax emulsion effective to suppress cracking, stem browning, and/or water loss according to the methods of the invention. In a fifth aspect, the invention provides compositions comprising a wax emulsion and an osmoregulator, as described above.

The following examples merely illustrate the best mode now contemplated for practicing the invention, but should not be construed to limit the invention.

EXAMPLE 1

The beneficial effects of a representative protective composition of the invention in decreasing both types of sunburn in field trials on 'Jonagold' apples are shown in Table 1. The composition was 5% w/w of Tixogel® MP100 in APL-BRITE 310 C (hereafter PFT-X). PFT-X was applied at full strength onto apple fruits. A single application of the protectant was made to 'Jonagold' apples at Wenatchee, Wash. on July 14. At the time of application no sunburn was observed on developing fruit. There was only one severe heat spell of sufficient intensity to cause the majority of sunburn during the growing season. It occurred during the first week of August. On August 19, apples treated with PFT-X had significantly less (P<0.05) sunburn necrosis and sunburn browning than did untreated control fruits. On September 10, sunburn necrosis was significantly lower in treated apples. The incidence of the necrosis type of sunburn was decreased by 66% on fruits treated with PFT-X in these field trials. The incidence of the surface browning type of sunburn ("buckskin") was decreased by 79%. Total sunburn was decreased by 73% in apples treated in accordance with the invention.

TABLE 1

Incidence of Sunburn Necrosis and Sunburn Browning as Influenced by PFT-X Formulation

| Fruit Variety | Observation Date | Incidence of Necrosis | | Incidence of Browning | |
|---|---|---|---|---|---|
| | | Control | Treated | Control | Treated |
| 'Jonagold' | 14 July | 0[1] | 0 | 0 | 0 |
| | 29 July | 6.7 | 5.0 | 6.7 | 0 |
| | 19 Aug. | 26.3 | 9.1* | 17.5 | 3.6* |
| | 10 Sept. | 25.9 | 8.8* | 6.9 | 0 |

[1]Each mean represents observations on 60 attached fruit that had been fully exposed to solar radiation for a daily duration of 3 hours before to 3 hours after solar noon. Controls received no application of the test formulation. Treated apples received one application of formulation.
*Denotes statistical significance of differences between control and treatment for each date as determined by a Yates-corrected z-test at the 0.05 level with n = 60.

EXAMPLE 2

The beneficial effects of a representative protective composition of the invention in decreasing sunburn in field trials on 5-year-old 'Jonagold' apples are shown in Table 2. The PFT-X composition was as listed in Table 1, but the formulation was diluted 1:1 with water before application to trees. Treatments were applied to single tree plots replicated ten times in a completely randomized design in the Clayton Orchard near Orondo, Wash. All treatments were applied with a handgun sprayer at approximately 150 pounds per square inch (psi) to near the point of drip, simulating a dilute spray of approximately 200 gallons/acre. For PFT-X, this provided 40 pounds of organoclay per acre and for Surround®, this provided 50 pounds of kaolin per acre. Each formulation was applied three times during the fruit growing season on July 7, August 4, and September 1. The control trees were sprayed with water on the same dates. For comparison, Surround®, a kaolin-based formulation containing proprietary surfactants and spreaders (marketed on a limited scale in by Engelhard Chemical Co., Iselin, N.J.) was applied in the same manner to another group of trees. Surround® was formulated as suggested by the manufacturer using M-03, a proprietary Spreader/Sticker. 450 ml of M-03 was added to 50 lbs of kaolin clay (Engelhard Chemical M-97-009) that had previously been added to 100 gallons of water in a recirculating sprayer tank.

The sunburn data are presented in Table 2. The incidence of sunburn in all treatments was evaluated on August 31 by evaluating all fruit on each tree in the experiment. The percent of sunburn incidence for each tree was calculated. Both sunburn necrosis and sunburn browning were evaluated, but the incidence of sunburn necrosis was so low (<7% of total sunburn) that the two types were combined and analyzed statistically. Data were transformed using the angular or inverse sine transformation method (Steel and Torrie, Principles and Procedures of Statistics, McGraw-Hill Book Co., Inc., New York) prior to an analysis of variance.

TABLE 2

Incidence of Sunburn as Influenced by PFT-X.

| | Incidence of Sunburn (%) | | |
|---|---|---|---|
| Fruit Variety | Control | Treated with PFT-X | Treated with Surround® |
| 'Jonagold' | 15.77 | 6.01** | 15.26 |

**Denotes statistical significance of differences between control and PFT-X at the 0.01 level.
Total number of fruit evaluated were 723, 649, and 557 for the control, PFT-X treated, and Surround®-treated apples, respectively.

The data in Table 2 indicate that apples treated in accordance with the invention showed significantly less sunburn than apples treated with water or Surround®.

EXAMPLE 3

The beneficial effects of a representative protective composition of the invention in decreasing sunburn in field trials on 3-year-old 'Cameo' apples are shown in Table 3. Sunburn damage was evaluated September 1. Other experimental details were the same as those in Example 2 except that trees were smaller, and two trees were included in each replication. The trees were in the Fleming Orchard near Orondo, Wash.

TABLE 3

Incidence of sunburn as influenced by PFT-X Application

| | Incidence of Sunburn (%) | | |
|---|---|---|---|
| Fruit Variety | Control | Treated with PFT-X | Treated with Surround® |
| 'Cameo' | 13.40 | 6.59** | 13.85 |

**Denotes statistical significance of differences between control and PFT-X at the 0.01 level.
Total number of fruit evaluated were 291, 260, and 258 for the control, PFT-X treated, and Surround®-treated apples, respectively.

The incidence of sunburn in 'Cameo' apples was reduced significantly when treated with the inventive PFT-X formulation as compared to apples treated with water or Surround® (Table 3).

EXAMPLE 4

The beneficial effects of a representative protective composition of the invention in decreasing sunburn in field trials on 9-year-old 'Fuji' apples are shown in Table 4. Sunburn damage was evaluated October 19. Other experimental details were the same as those in Example 2 except that a fourth application of formulations was made September 29. All fruit on two large branches of each tree were evaluated, as trees were much larger than those used in Examples 2 and 3. The trees were in the Fugachee Orchards near Pateros, Wash.

TABLE 4

Incidence of sunburn as influenced by PFT-X Application

| | Incidence of Sunburn (%) | | |
|---|---|---|---|
| Fruit Variety | Control | Treated with PFT-X | Treated with Surround ® |
| 'Fuji' | 14.85 | 2.44** | 8.59 |

**Denotes statistical significance between PFT-X and both control and Surround ® at the 0.01 level.
Total number of fruit evaluated were 485, 779, and 489 for the control, PFT-X treated, and Surround ®-treated apples, respectively.

The incidence of sunburn in 'Fuji' apples was reduced significantly when treated with the inventive PFT-X formulation as compared to apples treated with water or Surround® ((Table 4).

EXAMPLE 5

To evaluate the entomological efficacy of the inventive formulation PFT-X, a trial was conducted with 12-year-old 'Gala' apple trees at the Washington State University Tree Fruit Research & Extension Center, Wenatchee, Wash. Control of codling moth (*Cydia pomonella* L.)(CM) during their second generation was evaluated. PFT-X treatments were applied to single tree plots replicated five times in a randomized complete block. PFT-X was applied with a handgun sprayer at 300 psi to the point of drip, simulating a dilute spray of approximately 400 gallons/acre. Three different PFT-X and Surround® application protocols were tested:

1) trees were sprayed with PFT-X or Surround® three times during the CM oviposition period (July 19 [1,000 degree day total], July 27 and August 4);

2) trees were sprayed with PFT-X or Surround® three times during the CM hatch period (August 12 [1,250 degree day total], August 18 and 25); and 3) trees were sprayed with PFT-X or Surround® six times (all dates) covering the CM oviposition and hatch periods. For all PFT-X and Surround® application protocols a sample of fruits was harvested and an evaluation of CM insect damage to the fruit was made on September 1 by visually inspecting fifty apples per replicate and recording the number of stings and entries.

TABLE 5

Codling Moth damage to apple fruit as influenced by applications of PFT-X or Surround ® during oviposition, hatch, or oviposition + hatch.

| | Rate (Form./ | | #/50 fruit | | % total |
|---|---|---|---|---|---|
| Treatment | 100 gal) | Timing[1] | Stings | Entries | injury |
| Surround ® | 25 lbs | Oviposition | 0.8a[2] | 3.0bc | 7.6b |
| Surround ® | 25 lbs | Hatch | 0.8a | 4.0b | 9.6b |
| Surround ® | 25 lbs | Oviposition + hatch | 0.8a | 2.0bc | 5.6b |
| PFT-X | 20 lbs | Oviposition | 0.8a | 2.6bc | 6.8b |
| PFT-X | 20 lbs | Hatch | 1.2a | 2.2bc | 5.2b |
| PFT-X | 20 lbs | Oviposition + hatch | 1.4a | 0.2c | 3.2b |
| Untreated | NONE | | 0.8a | 12.2a | 26.0a |

[1]Application dates for Oviposition timing were Jul 19, Jul 27 and Aug 4 and for the Hatch timing were Aug 12, 18, and 25. Applications for the Oviposition + hatch timing included all six dates.
[2]Means in the same column followed by the same letter not significantly different (P = 0.05, Duncan's new multiple range test).

Both the PFT-X and Surround® treatments significantly reduced CM injury relative to the untreated control (Table 5). There was no difference in the number of CM stings (shallow unsuccessful entries) across treatments. Most of the effect of the treatments with both PFT-X and with Surround® was observed in the reduction of successful entries into fruit. There was no observed advantage of timing, but when applications were made to both the oviposition and hatch periods, the level of fruit injury was slightly lower than when treatments were applied to either the oviposition or hatch period. The formulations of the present invention show promise as tools to manage codling moth, probably as supplements to other "soft" tactics such as mating disruption. These data and the data presented in Tables 1–4 demonstrate that the inventive composition has dual benefits when applied to fruit trees. The inventive composition is effective at significantly reducing the incidence of fruit sunburn and reducing fruit damage caused by codling moth.

EXAMPLE 6

Some formulations cause phytotoxicity and others affect physiological processes such as photosynthesis when applied to trees. It has been shown that any unusual change in the overall bioenergetic status of the plant can be detected by a change in chlorophyll fluorescence (See generally, Lichtenthaler, K. K., "Applications of Chlorophyll Fluorescence in Photosynthesis Research, Stress Physiology," *Hydrobiology and Remote Sensing*, Kluwer Academic Publishers, Dordrecht, Germany (1988)). This includes all the reactions from the oxidation of water through electron transport, development of the electrochemical gradient, ATP synthesis, and eventually the series of enzymatic reactions for $CO_2$ reduction to carbohydrate in the leaf. Even changes in the plant that affect stoma opening and gas exchange with the atmosphere are reflected by changes in the fluorescence characteristics of a leaf. Therefore fluorescence was used as an indicator of any deleterious effects resulting from application of formulation. An OS5-FL Modulated Chlorophyll Fluorometer (Opti-Sciences, Inc. Tyngsboro, Mass.) was used to determine 'dark-adapted' Fv/Fm. Fv/Fm=Fm−Fo/

Fm where Fo and Fm are the minimal and maximal fluorescence yield of a 'dark adapted' sample. Leaves from the same trees and formulation treatments used in Example 4 were surveyed by fluorescence to obtain an estimation of electron flow in Photosystem II of photosynthesis. Fluorescence was determined on five attached leaves on trees in each of the five replications used in Example 4. On average, 84% of the incident quanta are absorbed by a leaf. Thus, a value for Fv/Fm of about 0.8 indicates healthy leaves with near maximal electron transport.

TABLE 6

Influence of PFT-X and Surround ® on fluorescence of leaves (estimation of electron flow in Photosystem II of photosynthesis).

| Treatment | Rate of (Form./ 100 gal) | Application Dates | Fluorescence (Fv/Fm) |
| --- | --- | --- | --- |
| Surround ® | 25 lbs | Jul 19, Jul 27, Aug 4 | 0.777 |
| Surround ® | 25 lbs | Aug 12, 18, and 25 | 0.797 |
| Surround ® | 25 lbs | Jul 19, 27; Aug 4, 12, 18, 25 | 0.816 |
| PFT-X | 20 lbs | Jul 19, Jul 27, Aug 4 | 0.808 |
| PFT-X | 20 lbs | Aug 12, 18, and 25 | 0.781 |
| PFT-X | 20 lbs | July 19, 27; Aug 4, 12, 18, 25 | 0.785 |
| Untreated | NONE | | 0.801 |

The results in Table 6 indicate that the inventive formulation had no significant effect on (P=0.05) fluorescence of the leaves to which formulation was applied. Thus, no evidence of damage to the overall bioenergetic status of the trees is seen with any of the formulations. No phytotoxicity to either fruit or leaves was observed with any formulations.

EXAMPLE 7

Before field testing, entomologists sometimes conduct bioassays to determine the inherent toxicity of new formulations, changes in behavior of insects exposed to new formulations, and appropriate concentrations to apply. Accordingly, the inventive PFT-X formulation was used in two bioassays.

Adulticide bean disk bioassay. Leaf disks (2 cm diameter) were cut from untreated leaves of bean (Phaseolus vulgaris 'Henderson Bush'). Disks were floated with the abaxial (lower) surface up in a ¾ounce plastic portion cup filled with cotton and distilled water. Twenty adult twospotted spider mites (TSM), (Tetranychus urticae Koch) were transferred to the lower surface with a fine paintbrush. The leaf disks containing mites were treated with five concentrations of PFT-X or a distilled water check.

All cups containing the five replicates of each treatment were treated at the same time in a Potter Spray Tower equipped with the intermediate nozzle, and set to 6.5 psi. Two ml of the pesticide solution were placed in the reservoir, and sprayed onto the disks. The mites were held in a growth chamber at 22±2° C. Mites were evaluated variously from 24 h after treatment for response as described immediately below.

| Category | Description |
| --- | --- |
| Alive | Moving without stimulation, or capable of moving >1 body length after gentle stimulation with brush. |
| Dead | No movement whatsoever, even after stimulation; or desiccated. |
| Moribund | Capable of producing some movement, especially twitching of legs, but unable to move >1 body length after stimulation. |
| Runoff | Found in cotton or water surrounding leaf surface, but not on leaf disk. Makes no difference if dead or alive. (If walk off occurs during the course of the evaluation, count as alive.) |

Table 7 presents the results obtained using the bean disk bioassay and PFT-X at a variety of application doses. PFT-X was applied to the bean disks and the evaluation for effects on mites was done 24 hours later. The full-strength PFT-X as described in Table 1 was diluted in distilled water to provide concentrations ranging from 100 to 700 grams of PFT-X per liter.

TABLE 7

Mortality and runoff resulting from treatment of twospotted spider mites on bean disks treated with PFT-X.

| Concentration (g/liter) | No. Subjects | % Mortality | % Runoff |
| --- | --- | --- | --- |
| 700 | 111 | 7.3 | 1.0 |
| 500 | 103 | 3.8 | 3.5 |
| 300 | 99 | 0.0 | 4.6 |
| 200 | 101 | 2.9 | 1.9 |
| 100 | 102 | 4.9 | 0.0 |
| 0 | 103 | 4.5 | 4.6 |

The results in Table 7 indicate that there was no dose response to the inventive PFT-X formulation after 24 h, either in terms of mortality or runoff.

Motile Stage Mortality and Behavior, Whole Plant Bioassay: Five leaves on each of six infested bean plants from the composite TSM colony were tagged. Prior to treatment, all motile stages were counted with a 5x-magnification headband (OptiVisor). Counts from the top and bottom side of the leaf were recorded separately. The same leaves were counted 24 h after treatment. Various concentrations of PFT-X were applied with a hand-pump-pressurized sprayer. The suspensions were kept under constant agitation during application. Five replicates were used for each treatment. Table 8 shows the data obtained from the whole plant bioassays with the inventive PFT-X formulation applied at a variety of concentrations. PFT-X was diluted as described in Table 7. Pre-treatment observations were made before application, and post-treatment observations were made 24 hours later. Primary data were analyzed using the General Linear Models Procedure of SAS (SAS 1988 (*Statistical Analysis Institute*, 1988; *SAS/Stat User's Guide*, Release 6.03 Edition; SAS Institute, Inc., Cary, N.C.)) using both a classification model (AOV) and numeric (regression).

TABLE 8

Location and mortality status of mites before and after treatment with the inventive formulation in a whole bean plant bioassay.

| | | Live | | | Dead | |
|---|---|---|---|---|---|---|
| Concn in g/liter | Total live mites/leaf | Total surface mites/leaf | Bottom surface mites/leaf | Top surface % mites | Top surface mites/leaf | Bottom surface mites/leaf |
| Pretreatment | | | | | | |
| 700 | 35.6a[1] | 5.8a | 29.8a | 17.2 | — | — |
| 500 | 33.6a | 4.8a | 28.8a | 15.9 | — | — |
| 300 | 35.8a | 8.4a | 27.4a | 22.2 | — | — |
| 200 | 35.6a | 8.0a | 27.6a | 23.6 | — | — |
| 100 | 38.2a | 9.8a | 28.4a | 30.4 | — | — |
| 0 | 29.0a | 12.6a | 16.4a | 42.9 | — | — |
| Post-treatment | | | | | | |
| 700 | 7.2a | 2.4a | 4.8a | 28.7 | 3.8 | 3.8 |
| 500 | 11.4a | 3.8a | 7.6a | 36.4 | 2.2 | 4.0 |
| 300 | 6.8a | 1.8a | 5.0a | 25.0 | 4.0 | 4.2 |
| 200 | 14.6a | 4.2a | 10.4a | 27.7 | 2.8 | 2.4 |
| 100 | 12.2a | 3.2a | 9.0a | 22.5 | 2.6 | 5.4 |
| 0 | 14.0a | 6.6a | 7.4a | 42.6 | 4.8 | 3.6 |

[1]Means in the same column followed by the same letter not significantly different.

Although there was a considerable decrease in mite population after treatment with PFT-X, this decrease was not related to concentration. No differences among the various concentrations of PFT-X occurred in any of the variables measured or calculated (Table 8). In addition to mortality, the behavior of the mites (i.e., occupation of the upper versus lower surface of the leaf) was observed. Normally, the TSM preferentially occupy the lower leaf surface, and most of the webbing is found there. Treatment with the PFT-X did not alter this pattern (Table 8). The relationship between concentration and percentage occupancy on the upper leaf surface was analyzed by regression analyses, but no significant relationship existed after the treatment (data not shown). In summary, PFT-X does not appear to affect either mortality or one aspect of behavior (leaf surface preference) of these mites.

EXAMPLE 8

The effects of the inventive formulation (PFT-X) on phytophagous mites and their natural enemies were examined in an apple orchard. Four-year-old 'Oregon Spur Delicious' apples were used. Treatments were applied with an air-blast sprayer calibrated to deliver 100 gallons per acre. PFT-X treatments were applied August 4. The plot originally had no mite populations, so the orchard was seeded with twospotted mites (*Tetranychus urticae* Koch) from a greenhouse colony and later with European red mites (*Panonychus ulmi* Koch) from another orchard. In addition, the plot was sprayed with Asana® 0.66EC (DuPont Co., Wilmington, Del.)(1 pint/acre) plus Lorsban® 50W (Dow Chemical, Midland, Mich.)(3 lbs/acre) to reduce codling moth populations in the plots. Post-treatment mite counts were taken every week until early fall. A sample of 20 leaves per plot was taken and kept cool during transportation to the laboratory. Mites were removed from the leaves with a leaf-brushing machine, and collected on a revolving sticky glass plate. Mites on the plate were counted with the aid of a stereoscopic microscope. Motile and egg stages of the pest mites European red mite, twospotted spider mite, and McDaniel spider mite (*Tetranychus mcdanieli* McGregor) were counted, along with motile and egg stages of the predatory mites *Typhlodromus occidentalis* (Nesbitt) and *Zetzellia mali* (Ewing). Motile stages only of apple rust mite, *Aculus schlechtendali* (Nalepa), were also counted. The eggs of twospotted spider mite and McDaniel mite could not be distinguished from one another, and were recorded as a single category (*Tetranychus* eggs).

Table 9 presents the phytophagous and predatory mite population data and the effects of spray applications of various formulations including the inventive PFT-X composition.

TABLE 9

Phytophagous and predatory mite populations before and after treatment with miticides and formulations.

| Treatment | Rate/acre | Aug 2 | Aug 11 | Aug 17 |
|---|---|---|---|---|
| | | Total tetranychids/leaf | | |
| PFT-X | 10 lbs. | 6.99a[1] | 6.92a | 20.51a |
| PFT-X | 20 lbs. | 7.75a | 9.95a | 10.04a |
| Surround® | 25 lbs. | 6.74a | 23.01a | 19.24a |
| Surround® | 50 lbs. | 13.51a | 8.91a | 22.13a |
| Orchex 796[2] | 1% | 9.09a | 21.25a | 6.70a |
| Pyramite® 60W[3] + Orchex 796 | 4.4 oz. + 0.25% | 8.14a | 5.83a | 11.89a |
| Check | — | 7.16a | 13.93a | 29.98a |
| | | Total predatory mites/leaf | | |
| PFT-X | 10 lbs. | 0.13a[1] | 0.13a | 1.30a |
| PFT-X | 20 lbs. | 0.00a | 3.59a | 0.00 |
| Surround® | 25 lbs. | 0.10a | 3.43a | 0.29a |
| Surround® | 50 lbs. | 0.00a | 0.04a | 0.38a |

TABLE 9-continued

Phytophagous and predatory mite populations before and after treatment with miticides and formulations.

| Treatment | Rate/acre | Aug 2 | Aug 11 | Aug 17 |
|---|---|---|---|---|
| Orchex 796 | 1% | 0.00a | 0.79a | 0.75a |
| Pyramite ® 60W + Orchex 796 | 4.4 oz. + 0.25% | 0.03a | 1.04a | 0.09a |
| Check | — | 0.18a | 0.09a | 0.33a |

[1]Data were analyzed using analysis of variance on each count date (PROC GLM; SAS Institute, 1988). Means were separated with the Waller-Duncan k-ratio t-test.
[2]Purchased from Exxon Company, U.S.A., Houston, TX.
[3]Purchased from BASF Agricultural Products, Research Triangle Park, NC.

The mite populations consisted primarily of twospotted mites (71% overall) with some European red mite, and occasionally, some McDaniel mite forming a proportion of the population. The predatory mite population was primarily *T. occidentalis* (82% overall), with the remainder of the population comprised of *Z. mali*. Populations began to rise in late July, and were at an appropriate level (3 to 8 mites/leaf) by early August. No statistical differences occurred among any of the treatments (including the untreated check) at any time during the course of the experiment, despite treatment means that ranged from 7 to 30 mites/leaf (Table 9).

Predatory mite populations were high but variable throughout the test. On the first post-treatment count date (Aug 11), the low rate of Surround® and the high rate of PFT-X had exceptionally high T occidentalis populations (Table 9). This is especially notable since Asana®, a chemical known for its toxicity to predatory mites, was being sprayed at intervals. The use of Asana® compromised the test for predator toxicity, but there was no evidence that any of the materials were acutely toxic to *T. occidentalis* and *Z. mali*.

An additional mite control variable, known as cumulative mite days (CMD) was calculated for the formulations indicated in Table 9. CMD was calculated for each formulation using the equation:

$$CMD = \Sigma 0.5(pop_1 + pop_2)(date_1 - date_2),$$

where $pop_1$ is the population (total tetranychids/leaf) on $date_1$ and $pop_2$ is the population (total tetranychids/leaf on $date_2$).

CMD represents a time-weighted measurement of the populations. The CMD for Pyramite®+Orchex (CMD=402) was lowest. The CMD was 423 for PFT-X (10 lbs./A), and 477 for PFT-X (20 lbs./A). The CMD for the check was 567. The CMD was 508 for Surround® (50 lbs./A) and 519 for Surround® (25 lbs./A). For Orchex 796, the CMD was 513. The CMD data above indicate that PFT-X seemed to provide some suppression of the leaf mite populations across the growing season.

In summary, the inventive formulation of PFT-X tested in Table 9 had no apparent toxicity on the mites or their predators. As expected, PFT-X did not cause mortality in the mites. However, it is particularly important that the inventive formulation does not kill the beneficial predators or repel them from the leaf's surface, as this result indicates that PFT-X will be useful in Integrated Pest Management (IPM). In IPM practices, a formulation is useful only if the formulation provides what is called "soft suppression" of pests. That is, the IPM formulation does not cause a significant disruption to the natural control processes by, for example, negatively impacting populations of beneficial organisms.

EXAMPLE 9

The effects of several formulations on leafhopper nymphs in an apple orchard (cv. 'Braeburn') near Quincy, Wash. were examined. Four replicates were used where each replicate consisted of three trees in a single row. Leafhopper nymphs were sampled by counting the nymphs on 20 leaves/tree. Populations were sampled weekly until the majority of the population had transformed to the adult stage. A single-spray program and a three-spray program were compared. The single-spray treatment and the first application of the three-spray program were applied on August 3, using a multiple tank air-blast sprayer calibrated to deliver 100 gallons/acre. The second and third sprays of the three-spray program were applied on August 12 and August 20. Table 10 presents the data obtained from this study.

TABLE 10

Leafhopper nymph populations before and after treatment with pesticides and formulations.

| Treatment | Rate/acre | No. appl. | July 29 | Aug 6 | Aug 9 | Aug 16 | Aug 23 | Aug 31 |
|---|---|---|---|---|---|---|---|---|
| | | | | | Leafhopper nymphs/leaf | | | |
| PFT-X | 20 lbs | 1 | 3.89a[1] | 1.99bcd | 0.91c | 3.86abc | 3.55ab | 1.10ab |
| PFT-X | 20 lbs | 3 | 3.54a | 2.81bc | 2.85a | 3.49abc | 3.40ab | 1.21ab |
| Surround ® | 50 lbs | 1 | 3.44a | 1.86bcd | 1.09bc | 2.38bc | 2.63ab | 1.36a |
| Surround ® | 50 lbs | 3 | 3.49a | 1.41cd | 1.08c | 1.88c | 2.01bc | 0.31b |
| Orchex 796 | 1% | 1 | 3.44a | 3.28b | 3.36a | 5.01ab | 4.15a | 1.65a |
| Pyramite ® 60W + Orchex 796 | 4.4 oz + 0.25% | 1 | 3.53a | 1.34cd | 2.46ab | 5.09ab | 3.73ab | 1.44a |

TABLE 10-continued

Leafhopper nymph populations before and after
treatment with pesticides and formulations.

| Treatment | Rate/acre | No. appl. | Leafhopper nymphs/leaf | | | | | |
|---|---|---|---|---|---|---|---|---|
| | | | July 29 | Aug 6 | Aug 9 | Aug 16 | Aug 23 | Aug 31 |
| Provado ® L6F[2] + Sylgard 309[3] | 6 fl oz + 4 fl oz. | 1 | 3.70a | 0.61d | 0.20c | 1.18c | 0.60c | 0.94ab |
| Check | — | — | 3.70a | 6.11a | 3.79a | 6.28a | 4.24a | 1.85a |

[1]Data were analyzed using analysis of variance on each count date (PROC GLM; SAS Institute, 1988). Means were separated with the Waller-Duncan k-ratio t-test. Means within columns not followed by the same letters are significantly different.
[2]Purchased from Bayer Corporation, Pittsburgh, PA.
[3]Purchased from Wilfarm, L.L.C., Gladstone, MO.

The inventive PFT-X formulation (single application on August 3) provided suppression of nymphs through August 9, but thereafter the population mean was not different from the check (Table 10). With the three-spray program, PFT-X significantly suppressed nymph populations only on August 6, although the population means for the nymphs were always lower than the check. Only the standard (Provado+ Sylgard) provided much knockdown and residual control.

Orchex 796, an oil used by some in IPM programs as a soft pesticide, was included in this test. It was different than the check only on August 6. Its suppression of nymph populations was therefore much like that of the inventive PFT-X formulation. Thus, the data presented in Table 10 indicate that the PFT-X formulation of the present invention can be used as a component of an integrated pest management program.

EXAMPLE 10

The beneficial effects of a representative protective composition of the invention in decreasing damage by deleterious insects to foliage and fruit is tested in field trials on (A) apples [cv. 'Delicious', 'Golden Delicious', 'Fuji', 'Cameo', 'Jonagold' and 'Gala'] with the following target insects: codling moth, leafrollers, leafhoppers, spider mites, aphids, leafminers, true bugs (Pentatomidae and Miridae), cutworms, fruit worms, apple maggot, cherry fruit fly and San Jose scale; and on (B) pears [cv. 'Bartlett' and 'd'Anjou'] with the following target insects: pear psylla, true bugs, cutworms, spider mites, mealybug, and codling moth. Initial tests are conducted with high-pressure handgun spray equipment using a spray volume equivalent to 100 to 400 gal/acre. The results obtained allow determination of an activity profile for the inventive formulation on the target insects. Increasing concentrations of Tixogel® MP 100 from 1 to 5% in APL-BRITE 310 C are used with aqueous dilutions of ½ to ¹⁄₁₀ strength to arrive at appropriate concentrations. Treatments are replicated three to six times in a randomized complete block design with single trees or small blocks of trees. An appropriate control consists of trees that receive no spray treatments. For entomological evaluations of pests on foliage, populations of insects such as mites, aphids, leafhoppers, pear psylla, and leafininers are evaluated pre-treatment and at intervals in the post-treatment period to determine efficacy. For pear psylla and other pests such as the codling moth, scale, and leafrollers, the level of injury to fruit is evaluated at three times during the growing season in each treatment by checking at least 25 fruit per tree (replicate).

EXAMPLE 11

This Example describes several factors that influence the rate and amount of cherry cracking.

1. Air Temperature vs. Cherry Fruit Surface Temperature

Thermocouples connected to a Campbell Scientific CR10X data logger were attached to 'Sweetheart' cherries to record fruit surface temperature on the southwest side of fruit (full sun exposure in afternoon) throughout the day at 5-minutes intervals. A thermocouple placed in the shade recorded air temperature. This study was conducted 3 weeks before fruit maturity on 'Sweetheart' cherries in a Wenatchee Heights orchard.

It was found that fruit surface temperature on the sun-exposed side of a cherry can be as much as 10° C. (18° F.) above air temperature. The differential between air and fruit temperature was larger than expected and helps explain why cherries are more likely to split when the sun comes out and air temperature rises rapidly after a rain.

2. Effect of Water Temperature on Cherry Cracking

Ninety 'Bing' cherries of uniform size and maturity were harvested and separated into nine sample lots of 10 each. Each lot was placed in a separate beaker containing deionized water. Three beakers were maintained at 40° C. (104° F.), three were maintained at 30° C. (86° F.), and three were maintained at 22° C. (72° F.). All fruits were examined at 30-minute intervals for cuticle cracking, and cracked fruits were removed from the beakers.

The effects of temperature are striking. At 104° F., all fruit cracked within 1.5 hours, whereas it took 3 hours at 86° F. and 6.5 hours at 72° F.

3. Effect of Water Quality on Cherry Cracking

'Bing' cherries of uniform size and maturity were harvested and separated into four lots of 30 each. Each lot was placed in a separate beaker. One beaker contained deionized water (DW) at 22° C. (72° F.); another contained city water (CW) at 22° C.; another contained a 10% (w/v) sucrose solution (SS) at 22° C.; and another contained irrigation water (IW) at 16° C. (61° F.). All fruits were examined at 30-minute intervals for cuticle cracking, and cracked fruits were removed from the beakers.

Water quality also affected cracking. Cracking was delayed by city water, irrigation water, and a sugar solution as compared to deionized water. The electrical conductivity of city water, irrigation water and sugar solution was considerable whereas deionized water was near zero.

4. Effect of Water Quality on Water Absorption in Cherries

'Bing' cherries of uniform size and maturity were harvested, separated into nine lots of 10 each, dipped in deionized water, blot dried, and weighed. Three lots were immersed in deionized water DW) at 22° C. (72° F.); three were immersed in city water (CW) at 22° C.; and three were immersed in 10% (w/v) sucrose solution (SS) at 22° C. Every 2 hours, each cherry lot was removed from solution, blot dried, reweighed, and recorded. Water absorption was calculated as percent change in weight.

Water absorption by 'Bing' cherries was also influenced by water quality. Water absorption was decreased by city water and sugar solution relative to deionized water.

EXAMPLE 12

This Example describes the effects of representative wax emulsions (Matrix I and Matrix II) of the invention on cherry cracking.

1. Effect of Matrix on Water Absorption in Cherries

The effect of Formulation II (C-Wax Emulsion, $CH_2O$ Inc., Olympia, Wash.) on water absorption in cherries was examined. Formulation II (also referred to herein as Matrix II) contains 10–20% refined carnauba wax, morpholine (<5%), and fatty acid (<5%) (Material Safety Data Sheet for C-Wax Emulsion, http://www.ch20.com/htmlmsds/35037445.htm). 'Bing' cherries of uniform size and maturity were harvested and separated into nine lots of 10 fruits each. Three lots were dipped quickly into 10% (v/v) Formulation II, three into 20% (v/v) Formulation II, and three into deionized water (DW). All fruits dried overnight at 22° C. and were weighed before immersion in DW. Every 2 hours, each cherry lot was removed from the DW, blot dried, and weighed. Water absorption was calculated as percent change in weight.

Water absorption was significantly decreased by applying Formulation II (Matrix II) to 'Bing' cherries before they were immersed in water, as shown in Table 11.

TABLE 11

Effect of Matrix on Water Absorption by Bing Cherries

| | Water Absorption (Percent Increase in Weight) | | |
|---|---|---|---|
| Time (hr) | Control | 10% Matrix II | 20% Matrix II |
| 0 | 0 | 0 | 0 |
| 2 | 3.03 | 1.64 | 1.89 |
| 4 | 3.86 | 2.28 | 2.45 |
| 6 | 4.78 | 2.89 | 3.03 |
| 8 | 5.63 | 3.52 | 3.27 |
| 11 | 7.21 | 4.67 | 4.31 |

Formulation II also substantially reduced cracking of 'Bing' cherries after 9 hours in water, as shown in Table 12.

TABLE 12

Effect of Matrix on 'Bing' Cherry Cracking

| | Percent Cracking of Cherries in Water | | |
|---|---|---|---|
| Time (hr) | De-ionized Water | 10% Matrix II | 20% Matrix II |
| 9 | 76.17 | 31.0 | 20.42 |
| 11 | 80.95 | 67.09 | 48.76 |

2. Effect of Matrix and Temperature on Cracking of Cherries at the Stem Bowl

'Bing' and 'Rainier' cherries of uniform size and maturity were harvested and separated into two lots of 60 for each cultivar. One lot of each cultivar was dipped into 20% (v/v) Formulation II (Matrix II), and the other was dipped into deionized water (DW). The fruit dried at room temperature overnight. The fruit pedicel (stem) of each cherry was cut so that only 0.5 cm remained. Plastic containers were prepared with four layers of absorbent paper; DW was added to a level sufficient to cover the paper and the cherry shoulders when they were immersed in an inverted position. Treated fruits and controls were maintained separately at 30° C. (86° F.) and 45° C. (113° F.) and were examined for cracking at 30-minute intervals.

For both 'Bing' cherries (Table 13) and 'Rainier' cherries (Table 14), cracking of the stem bowls was decreased and delayed by the application of Formulation II (Matrix II).

TABLE 13

Effect of Matrix and Temperature on Cracking of Stem Bowls of 'Bing' Cherries

| | Percentage of Cherries Cracked | | | |
|---|---|---|---|---|
| Time (hr) | Matrix II at 45° C. | Control at 45° C. | Matrix II at 30° C. | Control at 30° C. |
| 0.5 | | 0 | | |
| 1 | | 6.67 | | |
| 1.5 | 0 | 30 | | |
| 2 | 12.33 | 40 | | |
| 2.5 | 24.67 | 40 | | |
| 3 | 30 | 46.67 | | 0 |
| 3.5 | 46.67 | 73.33 | | 6.67 |
| 4 | 53.33 | 86.67 | | 13.33 |
| 4.5 | 66.67 | 93.33 | | 20 |
| 5 | 66.67 | 100 | 0 | 30 |
| 5.5 | 66.67 | | 6.67 | 40 |
| 6 | 66.67 | | 13.33 | 46.67 |
| 6.5 | 73.33 | | 26.67 | 53.33 |
| 7 | 80 | | 46.67 | 73.33 |

TABLE 14

Effect of Matrix and Temperature on Cracking of Stem Bowls of 'Rainier' Cherries

| | Percentage of Cherries Cracked | | | |
|---|---|---|---|---|
| Time (hr) | Matrix II at 45° C. | Control at 45° C. | Matrix II at 30° C. | Control at 30° C. |
| 3.5 | 0 | 0 | 0 | 0 |
| 4 | 0 | 20 | 0 | 0 |
| 4.5 | 10 | 40 | 0 | 0 |
| 5 | 10 | 40 | 0 | 0 |
| 5.5 | 30 | 60 | 0 | 0 |
| 6 | 30 | 80 | 0 | 10 |
| 6.5 | 30 | 80 | 10 | 20 |
| 7 | 40 | 90 | 20 | 40 |

3. Suppression of Cherry Cracking in the Field

Four 'Bing' cherry tress of uniform growth and vigor were selected. Three branches of each tree were sprayed 2 weeks before harvest with one of the following treatments: 10% (v/v) Formulation II (Matrix II), 20% (v/v) Formulation I (Matrix I), or DW (control). Formulation I comprises 5% carnauba wax, 3.45% oleic acid, 1.95% morpholine, and 89.6% water. Overhead sprinklers were installed in each tree, and deionized water was pumped through the nozzles with an electric pump to provide 0.4 gallons water/minute per nozzle. In some cases, four nozzles per tree were installed to wet the fruit for at least 2 hours. Fruits were evaluated for cracking the next day.

Cracking of 'Bing' cherries was significantly reduced by the two formulations (Matrix I and Matrix II). Formulation II reduced cracking from 29.6% in the control to 15.4% (P<0.01), and Formulation I decreased cracking to 9.3% (P<0.01). Cracking of 'Liberty Bell' was also significantly reduced by 20% (v/v) Formulation I (Matrix I). In addition to suppression of cracking, Formulation II (Matrix II) provides an attractive sheen on the cherries.

EXAMPLE 13

This Example describes the effects of a representative wax emulsion of the invention comprising one or more osmoregulators, such as salts, sugars, or amino acids on cherry cracking in several cherry cultivars.

The formulation of wax emulsion with and without osmoregulator(s) is sprayed on selected cherry trees of several cultivars in replicate studies. The concentration of osmoregulator(s) in the wax formulation is between about 0.01% and 5% (weight/volume). Deionized water is pumped through overhead sprinkler heads positioned to "rain" on the cherry trees to induce cracking. In addition, the treatments are evaluated for cherry cracking under conditions of natural rainfall.

A combination of the wax emulsion with one or more osmoregulators should be beneficial for suppressing cracking. It is hypothesized that the formulation will protect the osmoregulator(s) from being washed off the fruit and may cause a slow release of the osmoregulator(s). Thus, the formulation may serve several roles—i.e., to prevent rapid absorption of water through the cherry skin by repelling rainwater, to protect the osmoregulator(s) from being rapidly washed off the fruit, and possibly to cover or fill some of the tiny fractures in the fruit cuticle.

As an alternative to the "open" system, the trees are enclosed and overhead sprinklers in large Mylar bags similar to those used by Leo Lombardini and Matt Whiting for measuring photosynthesis are used ("closed" system). Enclosing the tree permits the saturation of the environment (i.e., increases the relative humidity to about 100%) around the tree and fruit with the deionized water applied overhead. If desired, fans are used to admit some drier air to provide various levels of relative humidity around the canopy and fruit. By monitoring the relative humidity, the level of relative humidity required for cracking can be established.

EXAMPLE 14

This Example describes the effects of a representative wax emulsion (Matrix II) of the invention on water loss from harvested cherries.

Two hundred 'Sweetheart' cherries of uniform size and maturity were harvested. The pedicel was removed from 100 of the cherries; 50 were immersed in 10% (v/v) Formulation II (see EXAMPLE 12) and 50 were immersed in DW. The other 100 fruits with pedicel attached were split and treated as above. All treatments were transported from the field to the laboratory (approx. 45 minutes), and then rinsed with DW, blot dried, grouped in lots of 10, and weighed. The various lots were held at 22° C. and reweighed at various times; the percent water loss was recorded as a percent change in weight.

The effect of Formulation II (Matrix II) on water loss is documented in Table 15. The green color of the stems was also examined, but differences were small. It should be noted, however, that the formulation was only on the fruit for 45 minutes before rinsing in order to simulate what a grower might experience when taking the fruit directly to storage. If the formulation is kept on the fruit longer or dried on the fruit, a bigger effect of the formulation on both stem color and water retention by the fruit is likely to be observed.

TABLE 15

Water Loss from Harvested 'Sweetheart' Cherries

Percent Decrease in Fresh Weight of Cherries Over Time in Storage

| Time (hr) | Matrix II with Stem | Matrix II no Stem | Control with Stem | Control no Stem |
| --- | --- | --- | --- | --- |
| 5 | 0.66% | 0.53% | 0.93% | 0.77% |
| 16 | 1.70% | 1.57% | 2.55% | 2.37% |
| 41 | 4.36% | 4.30% | 6.27% | 6.52% |
| 51 | 5.20% | 5.25% | 7.52% | 7.97% |
| 65 | 6.48% | 6.64% | 9.19% | 10.04% |
| 72 | 6.85% | 7.11% | 9.70% | 10.67% |

EXAMPLE 15

This Example describes the effects of a representative wax emulsion (Matrix III) of the invention on cherry cracking.

Three treatments were applied to 'Bing' cherry trees 2 weeks before maturity (pre-harvest) with a hand sprayer (at a rate comparable to 50 gal/acre) to different branches on a tree. Treatment 1 was with 10% Formulation III (Matrix III) (NS 9000, Pace International, Seattle Wash.), which comprises about 20% (w/v) carnauba wax and about 2 to 4% (v/v) each of morpholine and oleic acid; treatment 2 was with 20% Formulation III; treatment 3 was with water. After drying, the tree was enclosed in a Mylar canopy system, as described in EXAMPLE 13, supported by air pressure generated by an electric fan. A sprinkler system was installed inside the canopy and oriented to allow deionized water to be misted throughout the tree canopy. The water was cycled on/off to keep the cherry fruit surfaces wet as well as maintain high humidity and temperature within the Mylar canopy. A Campbell Scientific CR10 datalogger was used to collect fruit surface temperature, and ambient temperature inside and outside the canopy. A Hobo datalogger was used to record humidity inside the canopy. The canopy system was inflated during the day from early morning until sunset for 3 days. The deflated canopy was left in place over the cherry tree to maintain humidity overnight. Cherries were harvested from each treated branch the morning after the day when cracking was noted and the frequency for cracking was recorded.

The second experiment was performed 1 week before maturity (pre-harvest) was conducted using the same procedures as in the first experiment. Cherry cracking occurred during the first day. Fruit was harvested the next morning and percent cracking was recorded for each treatment.

Treatments 1–3 all reduced cracking frequency compared to the control treatment, when applied either 2 weeks or 1 week before maturity of the cherries, as shown in Table 16.

TABLE 16

Effect of Matrix III on Cherry Cracking

| Treatment | Percentage Cracking When Applied 2 Weeks Pre-Harvest | Percentage Cracking When Applied 1 Week Pre-Harvest |
| --- | --- | --- |
| Control | 39 | 42 |
| 10% Matrix II | 8 | 16 |
| 20% Matrix III | 24 | 25 |

EXAMPLE 16

This Example describes the relationship between cracking and water absorption in different cherry cultivars.

In studies to better understand the relationship between cracking and water absorption by cherries, cherries were immersed in deionized water, and weighed at 2-hour intervals to determine the amount of water absorbed. After 6 hours, 'Bing' had absorbed more (3.89% increase in fresh wt.) than either 'Van' (3.1%) or 'Lapins' (3.26%). To determine which parts of the cherries absorbed water, an experiment was conducted in which only the pedicels (stem) was immersed, pedicels and stem bowls were immersed, stylar ends only were immersed, and total fruits were immersed. No significant water uptake was recorded at the stylar scar end for 'Lapins' whereas water uptake at the stylar scar end of 'Van' and 'Bing' was 6% and 12%, respectively. This trend in stylar scar end water uptake corresponds with cracking resistance for these three cultivars with 'Lapins' more resistant than 'Van' and 'Bing' least resistant of the three (King & Norton (1987) *Fruit Varieties J.* 341:83–4; see also Lang et al. (1997) *Good Fruit Grower* 48(12):27–30). Other regions of the fruits' surface showed differences as well in water absorption.

Digital images taken with a Nikon SMZ-U dissecting microscope showed differences in the structure of the stylar scar end of each of the three cultivars. The junction between the stylar scar tissue and the cuticle appears to be open in the 'Bing', partially open in the 'Van' and closed in the 'Lapins'. "Conductive" tissue appears to be more pronounced in 'Bing', somewhat less in 'Van' and even less apparent in 'Lapins'. 'Rainier' cherries were also examined in this manner and also showed a tight junction between the stylar scar and the cuticle. Stylar scar appearance may change relative to maturity. However, these samples were representative of mature fruit at harvest.

The data from this study suggest that cherry cultivars have varying degrees of vulnerability to cracking depending on the location of the water/fruit surface interface. Fruit surface absorption was comparable in all three cultivars. Stylar scar end water uptake was higher in 'Bing' followed by 'Van' and 'Lapins'. The same trend is apparent in the stem bowl. During sustained rain exposure, the two regions of the cherry fruit which carry the highest water load are the stem bowl and the stylar scar end. Despite the closed appearance of the stylar scar, 'Rainier' cherries are thought to be highly susceptible to cracking (King & Norton (1987) *Fruit Varieties J.* 341:83–4).

Published studies of 'Sam' cherries treated with silicone to block water uptake showed no absorption from the stylar scar when the entire fruit was sealed except for the stylar scar (Beyer et al. (2002) *Hort. Sci.* 37(4):637–41). The 'Sam' cherry is a relatively crack resistant cultivar (King & Norton (1987) *Fruit Varieties J.* 341:83–4) which may have a stylar scar similar to other crack resistant cultivars, i.e., 'Lapins'. While these are not the only paths for water uptake in the cherry fruit, the specific differences in the cultivars described suggest an explanation for cracking susceptibility.

EXAMPLE 17

This Example describes the effects of a representative wax emulsion (Matrix III) of the invention on cherry firmness and stem browning.

1. Effect of Pre-Harvest Application of Matrix III and Calcium on Firmness. The effect of the Formulation III (Matrix III, see EXAMPLE 15) on cherry firmness was determined in the lab with a firmness meter. Firmness is a function of water content. Calcium chloride (0.5% w/v) was sprayed on two groups of trees 2 weeks before harvest. After drying, a 10% (v/v) dilution of Formulation III was applied to half of the trees. The calcium and Formulation III-treated cherries were firmer (279.8 mg/mm$^2$) after 12 days of cold storage (at 33° F.) compared to untreated control cherries (265.4 mg/mm$^2$) or cherries treated with calcium chloride alone (277.1 mg/mm$^2$). Increased firmness was also observed in a larger orchard trial with 'Bing' and 'Van' cherries.

2. Effect of Pre-Harvest Treatment With Matrix III on Stem Browning. 'Bing' cherries were sprayed 2 weeks prior to harvest with 10% or 20% Formulation III (Matrix III). They were stored at 33° F. for 12 days, and then evaluated for stem browning. The 10% and 20% Matrix III applications reduced stem browning by 23% and 28%, respectively, as compared to untreated control cherries.

3. Effect of Post-Harvest Treatment With Matrix III on Stem Browning. Cherries were treated with 10% Matrix III or a product containing sucrose esters (Semperfresh, Pace International, diluted according to label) shortly after harvest and placed in cold storage for 12 days (33° F.). Water loss and stem browning were evaluated and compared to untreated control cherries. Water loss was reduced 50% for cherries treated with 10% Matrix III and 40% for cherries treated with Semperfresh. Stem browning was reduced by 7% and 6% for cherries treated with 10% Matrix III or Semperfresh, respectively.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for suppressing water uptake in cherries, comprising applying to cherries at least two times at least two weeks before harvest an amount of wax emulsion effective to suppress water uptake, wherein the wax emulsion comprises carnauba wax, oleic acid, morpholine, water, and one or more osmoregulators selected from the group consisting of potassium nitrate and potassium chloride.

2. The method of claim 1, wherein the concentration of carnauba wax in the wax emulsion is from about 0.125% to about 25% (weight/weight).

3. The method of claim 1, wherein the concentration of oleic acid in the wax emulsion is from about 0.1% to about 16% (weight/weight) and the concentration of morpholine in the wax emulsion is from about 0.03% to about 6%.

4. The method of claim 1, wherein the wax emulsion comprises from about 0.125% to about 25% (weight/weight) of carnauba wax, from about 0.1% to about 16% (weight/weight) of oleic acid, from about 0.03% to about 6%

(weight/weight) of morpholine, and from about 53% to about 99.7% (weight/weight) of water.

5. The method of claim 1, wherein the concentration of the one or more osmoregulators is from about 0.01% to about 5.0% (weight/volume).

6. The method of claim 1, wherein the wax emulsion is applied to cherries before an anticipated rain fall.

7. The method of claim 1, wherein at least one application of the wax emulsion is applied to cherries at least 4 weeks before harvest.

8. The method of claim 1, wherein the one or more osmoregulators consists of potassium nitrate.

9. The method of claim 1, wherein at least one application of the wax emulsion is applied to cherries at least 3 weeks before harvest.

10. The method of claim 1, wherein at least one application of the wax emulsion is applied to cherries at least 2 weeks before harvest.

11. The method of claim 1, wherein the wax emulsion is applied to cherries at least three times before harvest.

12. The method of claim 1, wherein the wax emulsion is applied to cherries at least four times before harvest.

13. A method for suppressing stem browning in cherries, comprising applying to cherries at least two times at least two weeks before harvest an amount of wax emulsion effective to suppress stem browning, wherein the wax emulsion comprises carnauba wax, oleic acid, morpholine, water and one or more osmoregulators selected from the group consisting of potassium nitrate and potassium chloride.

14. The method of claim 13, wherein the wax emulsion comprises from about 0.125% to about 25% (weight/weight) of carnauba wax, from about 0.1% to about 16% (weight/weight) of oleic acid, from about 0.03% to about 6% (weight/weight) of morpholine, and from about 53% to about 99.7% (weight/weight) of water.

15. A method for suppressing water uptake in cherries, comprising applying to cherry trees at least four times at least two weeks before harvest an amount of wax emulsion effective to suppress water uptake, wherein the wax emulsion comprises carnauba wax, oleic acid, morpholine, potassium nitrate and water.

* * * * *